US010331146B2

(12) United States Patent
Rhodes et al.

(10) Patent No.: US 10,331,146 B2
(45) Date of Patent: Jun. 25, 2019

(54) CONTROL SYSTEM FOR RADIOPHARMACEUTICALS

(71) Applicant: Lantheus Medical Imaging, Inc., North Billerica, MA (US)

(72) Inventors: Derek F. Rhodes, North Andover, MA (US); Robert W. Siegler, Chelmsford, MA (US)

(73) Assignee: Lantheus Medical Imaging, Inc., North Billerica, MA (US)

(*) Notice: Subject to any disclaimer, the term of this patent is extended or adjusted under 35 U.S.C. 154(b) by 280 days.

(21) Appl. No.: 14/774,714

(22) PCT Filed: Mar. 14, 2014

(86) PCT No.: PCT/US2014/027807
§ 371 (c)(1),
(2) Date: Sep. 11, 2015

(87) PCT Pub. No.: WO2014/143725
PCT Pub. Date: Sep. 18, 2014

(65) Prior Publication Data
US 2016/0026193 A1 Jan. 28, 2016

Related U.S. Application Data

(60) Provisional application No. 61/801,461, filed on Mar. 15, 2013.

(51) Int. Cl.
*G06Q 50/22* (2018.01)
*G05D 21/02* (2006.01)
(Continued)

(52) U.S. Cl.
CPC .............. *G05D 21/02* (2013.01); *G05B 15/02* (2013.01); *G06Q 10/06* (2013.01); *G06Q 30/018* (2013.01); *G06Q 50/22* (2013.01)

(58) Field of Classification Search
CPC ...... G06Q 10/06; G06Q 50/22; G06Q 30/018; G05B 15/02; G05D 21/02
See application file for complete search history.

(56) References Cited

U.S. PATENT DOCUMENTS

| 5,143,081 A | 9/1992 | Young et al. |
| 5,761,064 A | 6/1998 | La et al. |

(Continued)

FOREIGN PATENT DOCUMENTS

| CN | 101493697 A | 7/2009 |
| JP | 2001-188876 A1 | 7/2001 |

(Continued)

OTHER PUBLICATIONS

Translation for JP2003-022115, Jan. 29, 2003.*
(Continued)

*Primary Examiner* — Shogo Sasaki
(74) *Attorney, Agent, or Firm* — Wolf, Greenfield & Sacks, P.C.

(57) ABSTRACT

Techniques for monitoring a pharmaceutical manufacturing process and making determinations regarding the release of radiopharmaceuticals to health care providers. A data processing system collects data across multiple batches of radiopharmaceuticals, across multiple entities, and/or across multiple stages of the manufacturing process, processes the data, and provides feedback to entities involved in the manufacturing process. In scenarios where quality assurance tests are conducted, data is collected from radiopharmaceutical products before they are shipped, and the data is analyzed to provide the recipients with an indication of whether the radiopharmaceutical products satisfy quality assurance standards. Techniques for analyzing information about a batch manufacturing process and, when a problem occurred during a manufacture of a batch, determining whether to continue to manufacture a next batch in time for (Continued)

delivering and administering to a patient. The detected problem may be investigated and remedied before or during the synthesis of the next batch.

22 Claims, 16 Drawing Sheets

(51) Int. Cl.
  *G06Q 10/06* (2012.01)
  *G06Q 30/00* (2012.01)
  *G05B 15/02* (2006.01)

(56) References Cited

U.S. PATENT DOCUMENTS

| | | | |
|---|---|---|---|
| 6,243,615 | B1 | 6/2001 | Neway et al. |
| 6,748,285 | B2 | 6/2004 | Bozich et al. |
| 7,275,070 | B2 | 9/2007 | Kataria et al. |
| 7,305,278 | B2 | 12/2007 | Enright et al. |
| 7,568,000 | B2 | 7/2009 | Keyes et al. |
| 7,799,273 | B2 | 9/2010 | Popp |
| 8,015,443 | B2 | 9/2011 | Adachi |
| 8,019,554 | B2 | 9/2011 | Conway et al. |
| 2003/0149608 | A1 | 8/2003 | Kall et al. |
| 2004/0117126 | A1 | 6/2004 | Fetterman et al. |
| 2004/0153868 | A1 | 8/2004 | Nonaka et al. |
| 2004/0236723 | A1 | 11/2004 | Reymond |
| 2005/0159973 | A1 | 7/2005 | Krause et al. |
| 2005/0251276 | A1 | 11/2005 | Shen |
| 2005/0251278 | A1 | 11/2005 | Popp |
| 2007/0142950 | A1 | 6/2007 | Okita |
| 2007/0179811 | A1 | 8/2007 | Reiner |
| 2007/0185751 | A1 | 8/2007 | Dempers |
| 2008/0091466 | A1 | 4/2008 | Butler et al. |
| 2008/0109232 | A1 | 5/2008 | Musgrove et al. |
| 2008/0154909 | A1 | 6/2008 | Dam et al. |
| 2008/0274510 | A1 | 11/2008 | Santi et al. |
| 2009/0149981 | A1 | 6/2009 | Evans et al. |
| 2009/0193049 | A1 | 7/2009 | Karimisetty et al. |
| 2009/0292156 | A9 | 11/2009 | Whittacre et al. |
| 2010/0161101 | A1 | 6/2010 | Pouyez et al. |
| 2011/0029445 | A1 | 2/2011 | Whittacre et al. |
| 2012/0078648 | A1 | 3/2012 | Reiner |

FOREIGN PATENT DOCUMENTS

| | | |
|---|---|---|
| JP | 2003-022115 A | 1/2003 |
| JP | 2010-507176 A | 3/2010 |
| WO | WO 2005/110543 A2 | 11/2005 |

OTHER PUBLICATIONS

International Search Report and Written Opinion for PCT/US2014/027807 dated Jul. 25, 2014.
International Preliminary Report on Patentability for PCT/US2014/027807 dated Sep. 24, 2015.
[No Author Listed], OSIsoft PI Historian—Application Summary. Automated Results Computer Consulting LLC. Brevard, NC. In existence as of Aug. 3, 2012. Last accessed Jun. 1, 2017 at <http://www.automatedresults.com/PI/pi-historian.aspx>. 2 pages.
Amadeo et al., Determination of Robustness and Optimal Work Conditions for a Purification Process of a Therapeutic Recombinant Protein Using Response Surface Methodology. Biotechnology Progress. May 2011;27(3):724-32.
Andraos, On using tree analysis to quantify the material, input energy, and cost throughput efficiencies of simple and complex synthesis plans and networks: Towards a blueprint for quantitative total synthesis and green chemistry. Organic Process Research & Development. Feb. 2006;10(2):212-40.
Christophe et al., To robotize chemistry laboratories. An example of organic synthesis: 2-Boc-amino-N-hydroxy-3-phenyl-propionamide. J Autom Methods Manag Chem. 2002;24(1):17-24. doi: 10.1155/S1463924602000032.
Enjalbal et al., MALDI-TOF MS analysis of soluble PEG based multi-step synthetic reaction mixtures with automated detection of reaction failure. Journal of the American Society for Mass Spectrometry. 2005;16(5):670-8.
Fassett, Key Performance Outcomes of Patient Safety Curricula: Root Cause Analysis, Failure Mode and Effects Analysis, and Structured Communications Skills. American Journal of Pharmaceutical Education. 2011;75(8):164. 6 pages.
Jeong et al., Synthesis of the Knowledge Model for Fault Diagnosis Using Qualitative Simulation. Korean J. Chem. Eng. Jan. 1993;10(1):36-43.
Kim et al., Development of a new automatic system for fault tree analysis for chemical process industries. Korean J. Chem. Eng. Nov. 2009;26(6):1429-40.
Kim et al., Risk Analysis Using Automatically Synthesized Robust Accident Scenarios and Consequence Assessment for Chemical Processes: Process Partition and Consequence Analysis Approach. Korean J. Chem. Eng. Nov. 2003;20(6):992-9.
Krouwer, An improved Failure Mode Effects Analysis for hospitals. Archives of Pathology and Laboratory Medicine. 2004;128(6):663-7.
Mila et al., Application of a risk analysis method to different technologies for producing a monoclonal antibody employed in Hepatitis B vaccine manufacturing. Biologicals. 2012;40(2):118-28.
Nam et al., Automatic Generation of the Symptom Tree Model for Process Fault Diagnosis. Korean J. Chem. Eng. Jan. 1993;10(1):28-35.
Oldenhof et al., Consistency of FMEA used in the validation of analytical procedures. Journal of Pharmaceutical and Biomedical Analysis. 2011;54(3):592-5.
Yeh et al., An automaton-based approach to evaluate and improve online diagnosis schemes for multi-failure scenarios in batch chemical processes. Chemical Engineering Research and Design. 2011;89(12A):2652-66.
Charoo et al., Quality by design approach for formulation development: A case study of dispersible tablets. International Journal of Pharmaceutics. 2012;423:167-78. Epub Dec. 23, 2011.
Cheng et al., Applying HFMEA to Prevent Chemotherapy Errors. J Med Syst. 2012;36:1543-51. Epub Nov. 11, 2010.
Mila et al., Using Quality Risk Management in the Plantibody HB-01 manufacturing by Transgenic Tobacco Plants for Vaccine Production. Lat Am J Pharm. 2010;29(3):383-92.
Silveira et al., Análisis modal de fallos y efectos del proceso de prescripción, validación y dispensación de medicamentos. Farmacia Hospitalaria. 2012;36(1):24-32. Epub Apr. 22, 2011.
Van Leeuwen et al., Risk analysis by FMEA as an element of analytical validation. Journal of Pharmaceutical and Biomedical Analysis. 2009;50:1085-7. Epub Jul. 7, 2009.

\* cited by examiner

| | | 1 |
|---|---|---|
| Low Chemical Yield ○ Yes ● No    Low Recovery ○ Yes ● No | | 1 |
| LOW CHEMICAL YIELD: | | |
| Production Operator assessment of reagents<br>A. Inspect reagents and all solutions made to determine if there is an obvious mistake in the:<br>1. Reagent Material<br>2. Solvents used to prepare reagent<br>3. Quantity of material used to make reagent solution<br>4. Expiry of material | | |
| ☑ Reagent materials correct | | TRUE |
| ☑ Solvents used to prepare reagents correct | | TRUE |
| ☑ Weighings and data entries appear correct | | TRUE |
| ☑ Reagents within expiry | | TRUE |
| ☑ No obvious reagent issues found | | TRUE |
| B. Inspect DSP and DSP acetonitrile solution to determine if there is an obvious mistake in the:<br>1. DSP<br>2. Solvents used to prepare the DSP solution<br>3. Quantity of material used to make DSP solution<br>4. Expiry of DSP or acetonitrile | | |
| ☐ DSP material correct | | FALSE |
| ☐ Acetonitrile used to prepare DSP solution correct | | FALSE |
| ☐ Weighings and data entries appear correct | | FALSE |
| ☐ DSP and acetonitrile within expiry | | FALSE |
| ☐ No obvious DSP solution prep issue | | FALSE |
| C. Inspect Acetonitrile wash solution to determine if there is an obvious mistake in the:<br>1. Acetonitrile correct grade<br>2. Acetonitrile free of obvious contamination<br>3. Acetonitrile within expiry | | |
| ☐ Acetonitrile used for wash is correct grade | | FALSE |
| ☐ Acetonitrile used for wash free of obvious contamination | | FALSE |
| ☐ Acetonitrile used for wash within expiry | | FALSE |
| ☐ No obvious Acetonitrile wash issue | | FALSE |
| D. Examine amount of 18F delivered to QMA and to Reactor: | | |
| ☐ mCi 18F delivered to QMA unusually low | | FALSE |
| ☐ mCi 18F delivered to Reactor unusually low | | FALSE |
| ☐ No obvious 18F delivery issue | | FALSE |
| Cyclotron assessment<br>A. Examine the following cyclotron parameters and operations:<br>1. Target<br>2. Beam time<br>3. Beam current<br>4. Volume O18 water used<br>5. Preparation of cyclotron lines (washes) | | |
| ☐ Correct target used | | FALSE |
| ☐ Beam time correct | | FALSE |
| ☐ Beam current correct | | FALSE |
| ☐ Volume O18 water correct | | FALSE |
| ☐ Target and cyclotron line washes performed correctly | | FALSE |
| ☐ No obvious cyclotron issues | | FALSE |

Fig. 8

Form 1: Issue Selection

| 1 | Low Chemical Yield |
|---|---|
| 2 | Low Recovery |
| 3 | F18 not delivered to reaction |
| 4 | No peaks on semi-prep HPLC |
| 5 | Low volume product |
| 6 | Other |

| Value Selected: | 1 |
|---|---|

Fig. 12

Form 2: Low Chemical Yield

| Reagents and Solutions | | Risk Value, No Mitigation | Risk Value, if Issue Ascribed | Assigned Risk, No Mitigation | Mitigation | Mitigation performed | Risk Value if Mitigated | Assigned Risk, After Mitigation |
|---|---|---|---|---|---|---|---|---|
| Material: | TRUE | 1 | 5 | 1 | Obtain new materials and make fresh | FALSE | 1 | 1 |
| Solvents: | TRUE | 3 | 5 | 3 | Obtain new materials and make fresh | FALSE | 1 | 3 |
| Quantity: | TRUE | 1 | 5 | 1 | Obtain new materials and make fresh | FALSE | 1 | 1 |
| Expiry: | TRUE | 1 | 5 | 1 | Obtain new materials and make fresh | FALSE | 1 | 1 |
| No issue: | TRUE | 1 | 5 | 1 | Obtain new materials and make fresh | FALSE | 1 | 1 |

| DSP and DSP acetonitrile | | Risk Value, No Mitigation | Risk Value, if Issue Ascribed | Assigned Risk | Mitigation | Mitigation performed | Risk Value if Mitigated | Assigned Risk, After Mitigation |
|---|---|---|---|---|---|---|---|---|
| DSP: | FALSE | 2 | 5 | 5 | Obtain different lot, or new sample | FALSE | 1 | 5 |
| Solvent: | TRUE | 3 | 5 | 3 | Obtain new material and make fresh | FALSE | 1 | 3 |
| Quantity: | TRUE | 2 | 5 | 2 | Make fresh DSP Solution | FALSE | 1 | 2 |
| Expiry: | TRUE | 1 | 5 | 1 | Obtain lot in date | FALSE | 1 | 1 |
| No issue: | TRUE | 2 | 5 | 2 | Obtain different lot, or new sample | FALSE | 1 | 2 |

C

| Acetonitrile Wash | | Risk Value, No Mitigation | Risk Value, if Issue Ascribed | Assigned Risk | Mitigation | Mitigation performed | Risk Value if Mitigated | Assigned Risk, After Mitigation |
|---|---|---|---|---|---|---|---|---|
| Grade: | TRUE | 1 | 3 | 1 | Obtain fresh bottle | FALSE | 1 | 1 |
| Contamination: | TRUE | 3 | 5 | 3 | Obtain fresh bottle | FALSE | 1 | 3 |
| Expiry: | TRUE | 1 | 3 | 1 | Obtain fresh bottle | FALSE | 1 | 1 |
| No issue: | TRUE | 2 | 3 | 2 | No mitigation required | FALSE | 1 | 2 |

Fig. 13-1

| F 18 Delivery | | Risk Value, No Mitigation | Risk Value, if Issue Ascribed | Assigned Risk | Mitigation | Mitigation performed | Risk Value if Mitigated | Assigned Risk, After Mitigation |
|---|---|---|---|---|---|---|---|---|
| QMA: | TRUE | 2 | 5 | 5 | Obtain different lot | FALSE | 1 | 5 |
| Cyclotron: | TRUE | 1 | 5 | 5 | ??? | FALSE | 1 | 5 |
| No issue: | TRUE | 1 | | 1 | No mitigation required | FALSE | 1 | 1 |

| Recipes | | Risk Value, No Mitigation | Risk Value, if Issue Ascribed | Assigned Risk | Mitigation | Mitigation performed | Risk Value if Mitigated | Assigned Risk, After Mitigation |
|---|---|---|---|---|---|---|---|---|
| Cleaning: | TRUE | 1 | 5 | 1 | Utilize correct cleaning recipe | FALSE | 1 | 1 |
| Production: | TRUE | 1 | 5 | 1 | Utilize correct production recipe | FALSE | 1 | 1 |
| No issue: | TRUE | 1 | 5 | 1 | No remediation required | FALSE | 1 | 1 |

| Nitrogen Gas | | Risk Value, No Mitigation | Risk Value, if Issue Ascribed | Assigned Risk | Mitigation | Mitigation performed | Risk Value if Mitigated | Assigned Risk, After Mitigation |
|---|---|---|---|---|---|---|---|---|
| Is leak: | TRUE | 1 | 5 | 5 | Fix leak | FALSE | 1 | 5 |
| Tubing: | FALSE | 1 | 5 | 1 | Replace tubing | FALSE | 1 | 1 |
| O-ring: | TRUE | 1 | 5 | 1 | Replace o-ring | FALSE | 1 | 1 |
| Vial seating: | TRUE | 1 | 5 | 1 | Insure vials seated correctly | FALSE | 1 | 1 |
| Valve leak: | TRUE | 2 | 5 | 2 | Fix valve | FALSE | 1 | 2 |

Fig. 13-2

| Gas Flow | | Risk Value, No Mitigation | Risk Value, if Issue Ascribed | Assigned Risk | Mitigation | Mitigation performed | Risk Value if Mitigated | Assigned Risk, After Mitigation |
|---|---|---|---|---|---|---|---|---|
| Slow: | TRUE | 1 | 5 | 5 | Perform maintenance | FALSE | 1 | 5 |
| Regular: | FALSE | 1 | 3 | 1 | Replace regulator | FALSE | 1 | 1 |

| Heating | | Risk Value, No Mitigation | Risk Value, if Issue Ascribed | Assigned Risk | Mitigation | Mitigation performed | Risk Value if Mitigated | Assigned Risk, After Mitigation |
|---|---|---|---|---|---|---|---|---|
| Set point | TRUE | 1 | 5 | 1 | Adjust setpoint | FALSE | 1 | 1 |
| Calibration current | TRUE | 1 | 3 | 1 | Recalibrate | FALSE | 1 | 1 |
| Calibration correct | TRUE | 1 | 5 | 1 | Recalibrate | FALSE | 1 | 1 |
| Heating element | TRUE | 1 | 5 | 1 | Replace heating element | FALSE | 1 | 1 |
| Heating controller | TRUE | 1 | 5 | 1 | Replace or repair controller | FALSE | 1 | 1 |

Fig. 13-3

| Vacuum | | Risk Value, if Issue Ascribed | Assigned Risk | Mitigation | Mitigation performed | Risk Value if Mitigated | Assigned Risk, After Mitigation |
|---|---|---|---|---|---|---|---|
| Vacuum functional | TRUE | 5 | 2 | Fix vacuum pump | FALSE | 1 | 2 |

| Overall Heat, Cool and Vacuum | | Risk Value, if Issue Ascribed | Assigned Risk | Mitigation | Mitigation performed | Risk Value if Mitigated | Assigned Risk, After Mitigation |
|---|---|---|---|---|---|---|---|
| No issue | TRUE | 1 | 1 | Remediate issue | FALSE | 1 | 1 |

Fig. 13-4

CONTROL SYSTEM FOR RADIOPHARMACEUTICALS

RELATED APPLICATIONS

This application is a national stage filing under 35 U.S.C. § 371 of International Application No. PCT/US2014/027807, filed Mar. 14, 2014, which was published under PCT Article 21(2) in English, and which claims the benefit under 35 U.S.C. § 119(e) of U.S. Provisional Application Ser. No. 61/801,461, entitled "CONTROL SYSTEM FOR RADIOPHARMACEUTICALS" filed on Mar. 15, 2013, the entire contents of both of which are incorporated herein by reference.

BACKGROUND

Radiopharmaceuticals are radioactive pharmaceutical agents that are introduced into a patient's body and enable various medical imaging and analysis procedures. Radiopharmaceuticals are typically administered in small amounts, and are designed to decay quickly inside the body to pose minimal harm to patients. Radiopharmaceuticals are often used to diagnose and/or treat medical conditions, for example in imaging studies of internal organs. The dispensing of radiopharmaceuticals is typically carried out at radiopharmacies, which typically receive various pharmaceutical compounds from different pharmaceutical manufacturing facilities (PMFs). Radiopharmaceuticals are typically synthesized at PMFs from different pharmaceutical compounds and radioactive isotopes, and dispensed by radio pharmacies to medical facilities and doctors for administration to patients.

SUMMARY

Due to the short half-life of their constituent radionuclides, radiopharmaceuticals are typically prepared on an as-needed basis and are intended for use within a short time post-synthesis (e.g., within hours post-synthesis). There is typically a small window of time between the synthesis of a radiopharmaceutical and its administration in a subject. During this time, radiopharmacies usually test the radiopharmaceutical to ensure its suitability for administration to patients before delivering the radiopharmaceutical to a hospital or other administration setting.

The inventors have recognized and appreciated techniques for quickly and accurately identifying problems in the manufacture of radiopharmaceuticals, and that such techniques may enable the safe administration of radiopharmaceuticals to patients. In some embodiments, these techniques may enable quality assurance tests to be performed without significantly delaying the shipment of the short half-life radiopharmaceuticals to patients.

The inventors have also recognized and appreciated that information about a process of manufacturing a radiopharmaceutical in batches may be utilized to more efficiently manage the manufacturing process and to comply with good manufacturing practices (GMPs) and any other guidelines for manufacturing of radiopharmaceuticals. The information may be used to identify problems during synthesis in batches and decrease overall risk of failures, thus saving time and resources. In particular, one or more characteristics of a process of manufacturing a batch may indicate whether a problem occurred during the manufacture of the batch A set of items, including potential problems, to be investigated upon a completion of a batch may be determined in advance and the one or more characteristics may be compared to the items, which may also be referred to as a checklist. The checklist may be generated in accordance with GMP. When a problem that occurred during manufacturing of the batch at a manufacturing facility is identified based on the comparison, it may further be determined whether to proceed to a synthesis of a next batch or to stop the manufacturing process and remedy the identified problem. The decision on whether to proceed with manufacturing a next batch may be made within a short period of time—for example, within an hour from the completion of a previous batch. Information about the detected problem, the decision made based on the problem and underlying logic may be represented as a report that may be generated in accordance with GMP and may be used by the manufacturing facility as evidence of compliance with the GMP.

Some embodiments are directed to a method of managing a pharmaceutical manufacturing process in which each of a plurality of entities performs at least a portion of the manufacturing process at a facility operated by the entity. The method comprises: at a data processing location, receiving data from each of the plurality of entities, the data relating to performance of the at least a portion of the manufacturing process at a manufacturing facility of the entity; with at least one processor at the data processing location, generating information about the manufacturing process based on the received data; and using the generated information to produce an output indicating a characteristic or adjustment to at least a portion of the manufacturing process as implemented by at least one of the plurality of entities;

Some embodiments are directed to a method of dispensing pharmaceutical products that undergo quality assurance tests prior to administration, wherein the pharmaceutical products degrade over a time commensurate with the duration of the quality assurance tests. The method comprises: initiating quality assurance tests on a pharmaceutical product; electronically collecting data relating to the quality assurance tests on the pharmaceutical product; analyzing the collected quality assurance data to produce an indication of whether the pharmaceutical product meets quality assurance standards; shipping the pharmaceutical product directed to an administration site prior to producing the indication; and after the shipping, sending an electronic communication directed to the administration site including the indication of whether the pharmaceutical product meets quality assurance standards.

Some embodiments are directed to a system for use in manufacturing a pharmaceutical. The system comprises: a database configured to store data; at least one processor connected to a network, wherein the processor is programmed to: receive data from each of a plurality of entities that performs at least a portion of a manufacturing process for a pharmaceutical at a facility operated by the entity, the data relating to performance of the at least a portion of the manufacturing process performed at a manufacturing facility of the entity; store at least part of the received data in the database; generate information about the manufacturing process based on the received data; and using the generated information, produce an output indicating a characteristic or adjustment to at least a portion of the manufacturing process as implemented by at least one of the plurality of entities.

Some embodiments are directed to at least one non-transitory computer-readable storage medium comprising computer-executable instructions that, when executed by at least one processor, perform a method comprising: receive data from each of a plurality of entities that performs at least a portion of a manufacturing process for a pharmaceutical at a facility operated by the entity, the data relating to performance of the at least a portion of the manufacturing process performed at a manufacturing facility of the entity; generate information about the manufacturing process based on the received data; and using the generated information, produce an output indicating a characteristic or adjustment to at least a portion of the manufacturing process as implemented by at least one of the plurality of entities.

Some embodiments are directed to a method of managing a process of manufacturing a plurality of batches of a radiopharmaceutical at a facility, the method comprising: receiving data relating to performance of the process of manufacturing a first batch of the plurality of batches of a radiopharmaceutical; with at least one processor, generating information about the process of manufacturing the batch; determining whether a problem occurred during the process of manufacturing the first batch using the generated information; when it is determined that the problem occurred during the process of manufacturing the batch, analyzing the problem to determine whether to proceed to a manufacture of a next batch; and generating an indication based on the analysis of the problem.

Some embodiments are directed to a method of managing a process of manufacturing a plurality of batches of a radiopharmaceutical at a facility, the method comprising: receiving data relating to performance of the process of manufacturing a first batch of the plurality of batches of a radiopharmaceutical; and, with at least one processor, within a time period after the process of manufacturing the first batch is completed: generating information about the process of manufacturing the batch; determining whether a problem occurred during the process of manufacturing the first batch using the generated information; when it is determined that the problem occurred during the process of manufacturing the batch, analyzing the problem to determine whether to proceed to manufacture a next batch; and generating an indication based on the analysis of the problem.

Some embodiments are directed to at least one non-transitory computer-readable storage medium comprising computer-executable instructions that, when executed by at least one processor, perform a method comprising: receiving information relating to performance of a process of manufacturing a first batch of a plurality of batches of a radiopharmaceutical; determining whether a problem occurred during the process of manufacturing the first batch using the information; when it is determined that the problem occurred during the process of manufacturing the batch, analyzing the problem to determine whether to proceed to a manufacture of a next batch; and generating an indication based on the analysis of the problem.

The method is performed in some instances in less than 6 hours, less than 3 hours, less than 2 hours, or less than 1 hour. In some embodiments, the method comprises evaluating a number of parameters of the first manufacturing process based on a binary response system (e.g., yes or no), and taking remedial action(s) based on response relating to one or more parameters.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 8 is a sketch of an example of a checklist that may be used for assessment of a performance of a process of manufacturing a batch of a PET pharmaceutical, in accordance with one embodiment;

FIG. 12 is an exemplary data capture form. Illustrated is an issue selection form.

FIG. 13 is an exemplary data capture form. Illustrated is a low chemical yield form.

DETAILED DESCRIPTION

Figure 1:
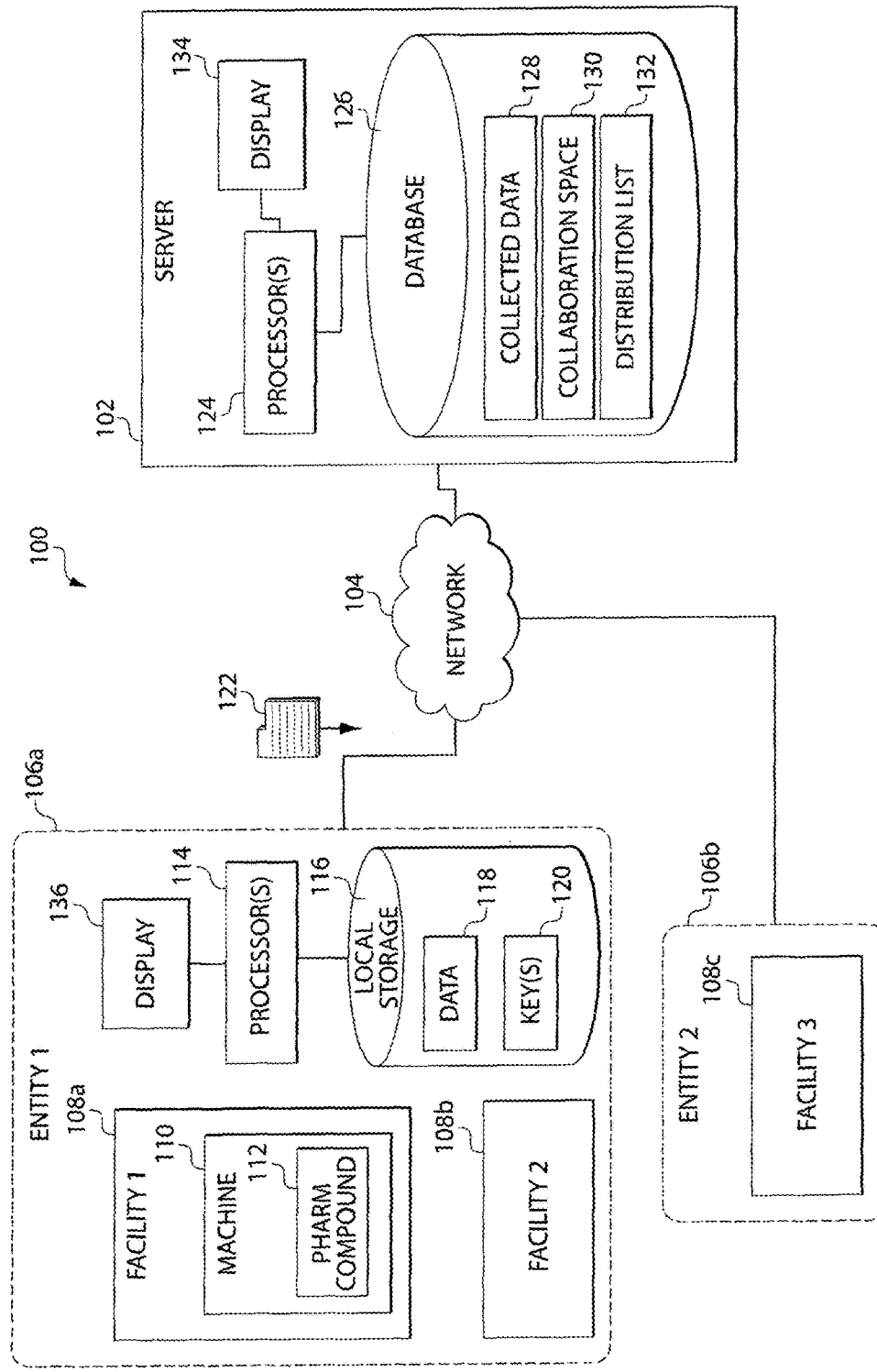
FIG. 1 is a schematic illustration of a system for monitoring, analyzing, and managing a pharmaceutical manufacturing process, according to some embodiments.

The inventors have recognized and appreciated that significant improvements in the safety and efficiency of synthesizing radiopharmaceuticals may be achieved by methods and systems for monitoring a pharmaceutical manufacturing process, making determinations regarding the release of radiopharmaceuticals to a health care provider, and providing feedback regarding the determinations. In some embodiments, the data processing system may collect data across multiple batches of radiopharmaceuticals, across multiple entities, and/or across multiple stages of the manufacturing process, the system may analyze the data, and provide a mechanism for feedback of the analysis to entities involved in the manufacturing process.

Accordingly, methods and systems described herein may be used for monitoring radiosynthesis at a pharmaceutical manufacturing facilities (PMF) over a period of time or over a number of syntheses. This latter type of monitoring may be used, in some embodiments, to monitor radiosynthesis trends at a PMF or at a number of PMFs, which may then be used to identify current infirmities or to predict future infirmities in the radiosynthesis processes and/or at particular PMFs.

The inventors have recognized and appreciated that by collecting and analyzing data across diverse collection points in the manufacturing process, significant improvements may be achieved in the speed and accuracy of identifying and/or predicting problems in the manufacturing process.

The inventors have also recognized and appreciated that collected data about a manufacturing process may be used to identify problems that occurred during a manufacture of a batch (or lot) of a pharmaceutical and use the information about the problems to make decisions regarding whether to proceed to synthesize a next batch or stop the manufacturing process. Radiopharmaceuticals are typically prepared on as-needed basis and a PMF may receive one or more orders that may require manufacturing a radiopharmaceutical within a short in time period after the synthesis. Thus, to fulfill the orders, the manufacturing facility may synthesize a radiopharmaceutical in batches, where a next batch is synthesized shortly after a previous batch is completed. If a problem occurs during a manufacture of a batch, an investigation and remediation of the problem may take time which may lead to a failure to proceed to a synthesis of the next batch.

Accordingly, techniques are provided for identifying a problem in the manufacture of a batch, analyzing the problem and making decisions regarding the manufacturing process based on the analysis. In particular, information about the problem may be used to determine whether the nature of the problem is such that it may be remedied in a timely manner and a synthesis of the next batch may begin without a delay. Furthermore, in some scenarios, it may be determined that the manufacturing process may continue to the next batch and a remediation of the problem may take place during a time when the next batch is synthesized. However, when the detected problem indicates that a problem may occur during a synthesis of the next batch, the analysis of the problem may indicate that there is a need to stop the manufacturing process and not proceed to the next batch. Investigation of the detected problem may then be conducted and the problem may be remedied. Information about the detected problem and the investigation may be represented as a report that may be generated in accordance with GMP. The manufacturing facility may use the report as evidence of compliance with the GMP.

The decision on whether to proceed with manufacturing a next batch may be made within a short period of time—for example, within an hour from the completion of a previous batch. Though, other time periods may be substituted as embodiments described herein are not limited in this respect. In this way, when a detected problem is determined not to affect the synthesis of the next batch, the next batch may be synthesized in a timely manner so that the manufactured radiopharmaceutical may be delivered and safely administered to a patient. However, when the detected problem indicates that a problem may occur during a synthesis of the next batch, the manufacturing process may not proceed to the next batch. Investigation of the detected problem may then be conducted.

In some embodiments, one or more characteristics of a process of manufacturing a batch may indicate whether there is a problem during a manufacture of a batch. A set of items used to analyze information about a manufacturing process may be determined in advance and the one or more characteristics may be compared to such set, which may also be referred to as a checklist. It may then be determined, based on the comparison, whether a problem occurred during the manufacture of the batch. The set of potential problems may include problems that may happen with any component of the manufacturing process and at any point during the process.

Each potential problem in the checklist may be associated with a risk posed by the problem and information on one or more remediation measures that may mitigate the problem. Risks associated with the identified problem and remediation measures may thus be determined based on the set of the potential problems. If the associated risks are severe and the problem requires remediation measure(s) that may not be completed in time for a synthesis of the next batch, the analysis of the problem may indicate that there is a need to stop the manufacturing process and remedy the identified problem. If the problem does not pose a risk of a failure during synthesis of a next batch or a risk may be remedied before the synthesis of the next batch, an indication may be provided instructing the manufacturing process to proceed to the subsequent batch.

FIG. 1 is a simplified illustration of an example of a system 100 for managing a pharmaceutical manufacturing process, according to some embodiments. The managing may include monitoring, analyzing, providing feedback to adjust the process and/or perform other actions. In the example of FIG. 1, a data processing location, such as server 102, receives data via a network 104, which may be a computer communications network, from a plurality of entities, such as entities 106a and 106b, involved in the pharmaceutical manufacturing process. The data may be pushed by the entities 106a and 106b to the server 102, and may be related to performance of different portions of the manufacturing process at one or more facilities of the entities, such as facilities 108a, 108b, and 108c. Although the example of FIG. 1 illustrates a single server 102, an entity 106a with two facilities, 108a and 108b, and an entity 106b with one facility 108c, it should be appreciated that embodiments are not limited to any particular number of servers, entities, or number of facilities therein.

In some embodiments, one or more entities, such as entity 106a of FIG. 1, may have pharmaceutical manufacturing facilities (PMFs), such as facilities 108a and 108b, that manufacture pharmaceutical compounds that are used to synthesize radiopharmaceuticals. In some embodiments, one or more entities, such as entity 106b in FIG. 1, may be a radio pharmacy that distributes radiopharmaceutical products to medical facilities for patient administration. In some embodiments, the server 102 may be operated by an entity that is separate from the entities 106a and 106b, although embodiments are not limited to this scenario, as the same entity may operate a data processing location along with one or more facilities involved in the manufacturing process.

In some embodiments, the collected data may relate to the performance of one or more machines in the facilities, such as machine 110 in manufacturing facility 108a of FIG. 1. A machine may be a device to heat, mix or otherwise process ingredients forming a pharmaceutical compound. Alternatively or additionally, the machine may be a measuring device or computer used in process control or any other device. In the example of FIG. 1, the machine 110 manufactures batches of a pharmaceutical compound 112 that is used to synthesize a radiopharmaceutical product. In this example, the manufacturing entity 106a may have one or more local processors, such as processor(s) 114, that gathers data from various machines in facilities of the entity 106a, such as machine 110. The entity 106a may also have a local repository, such as local storage 116, that stores data 118 related to the portion of the manufacturing process performed at manufacturing facilities of entity 106a. The local storage 116 may also store, among other things, one or more security keys, such as key(s) 120, that enable the entity 106a to push data to, and/or receive information from, the server 102. As non-limiting examples, security keys may comprise an executable, a license, a username/password, a device, a firewall, or any other suitable technique for limiting access to authorized entities.

In some embodiments, the data processing location, such as server 102, may collect data that is pushed from multiple entities. The data may relate to a plurality of batches of pharmaceutical compounds manufactured across multiple entities. Additionally or alternatively, the data may be collected from one or more radio pharmacies and may relate to at least one of drug dosage, customers, shipping, invoices, ordering, and/or commercialization. In general, the data processing location, such as server 102, may receive data collected across multiple batches of pharmaceutical products, across multiple entities, and/or across multiple stages of the manufacturing process. As such, the server 102 may be able to identify manufacturing problems more quickly than a single manufacturing site could, by aggregating data across multiple collection points throughout the manufacturing process.

The entities 106a and 106b may be configured to push data to the data processing location (e.g., server 102) for various reasons, such as security firewalls at the entities through which access may be difficult or cumbersome to obtain. But regardless of the reasons for pushing data from the entities 106a and 106b, data may be received at the server 102 in a format as a plurality of files, an example of which is shown as file 122 in FIG. 1. It should be appreciated, however, that embodiments are not limited to formatting data as files, and that any suitable data format may be used, depending, for example, on the format of data generated from batch production at the manufacturing entities, such as entity 106a.

Regardless of the exact nature and format of the data collected about the manufacturing process, server 102 may use at least one processor, such as processor(s) 124, to aggregate, store, and process the collected data. In some embodiments, the server 102 may populate a database, such as database 126, with the collected data, shown as stored collected data 128. The processor 124 may analyze the collected data to generate information about the manufacturing process based on the data. The information may be generated based on any suitable analysis technique, including but not limited to, trend analysis, release type parameters, identification of process parameter excursions that lead to out of specification results, etc.

In some embodiments, the analytics may comprise using statistical analysis and/or generating a trend analysis of at least one parameter of the manufacturing process, based on the collected data. The analysis may use data that is collected across a plurality of batches of a pharmaceutical compound manufactured at facilities associated with multiple entities. In some embodiments, the data may be associated with customer information and/or dosage information provided by one or more radio pharmacies. Regardless of the exact source(s) of data, in some embodiments, by aggregating and analyzing data across multiple batches and/or across multiple sites, the analysis may better enable predicting an area of concern before it actually takes place.

Using the analyzed information, the data processing location may produce an output indicating a characteristic or adjustment to the manufacturing process, as implemented by the entities. The output may be fed back to the entities to appropriately adjust their portions of the manufacturing process. For example, the output may comprise information defining a change in a recipe for synthesizing radiopharmaceuticals at a PMF. The server 102 may provide the feedback not only to the entities that pushed data, but also to any other suitable entity authorized to receive the feedback.

The feedback may be provided by any suitable electronic information-sharing mechanism. For example, in some embodiments, the feedback may be provided via an electronic posting to a collaboration space, such as collaboration space 130, that is accessible to one or more entities. A collaboration space may be implemented on an internet connected server by creating web pages that are accessible to collaborators for posting information and accessing posted information. Such a collaboration space may be implemented in any suitable way, including technology as known in the art. In some embodiments, the server 102 may electronically route a message containing the feedback to a stored distribution list, such as distribution list 132 in FIG. 1. In some embodiments, the feedback may be provided via email. Regardless of the exact technique used to provide feedback to the entities involved in the manufacturing process, in some embodiments, it may be desirable to provide the feedback in a human readable form.

The feedback may be displayed via one or more displays. For example, the server 102 may have a display 134 for outputting the information to a suitable administrative personnel or authority. Additionally or alternatively, an entity, such as entity 106a, may have a display 136 for outputting the feedback information to a worker at manufacturing facility 108a. It should be appreciated, however, that embodiments are not limited to displaying the feedback at manufacturing facilities or data processing locations, as the feedback may be provided to any suitable entity, such as a radio pharmacy dispensing radiopharmaceuticals, or a medical facility receiving a shipment of radiopharmaceuticals.

The display of the feedback, such as display 134 and/or 136, may display any suitable information contained in the feedback from the server 102. For example, the displays 134 and/or may show a web portal for the collaboration space 130, and/or may show instructions from an email sent to distribution list 132. Regardless of the exact content that is shown in the displays 134 and/or 136, the displays 134/136 may be used to show the information that was generated by the server 102, indicating a characteristic or an adjustment to at least a portion of the manufacturing process as implemented by at least one entity that pushed data to the server 102.

In some embodiments, it may be desirable to restrict access to the feedback information to only authorized entities. Security keys, such as security key 120 at entity 106a, may be used to enable such restricted access in a variety of different points in the system 100. For example, security keys may be used to restrict data that is pushed into the server 102 by entities 106a and 106b and/or to restrict information that is fed back from the server 102 back to the entities 106a and 106b. As a simple example, access to the shared collaboration space 130 may be restricted by security keys such as a username and password. Other examples of security keys will be presented in connection with FIG. 2, but in general, using security keys may enable the system 100 to implement a flexible, easy-to-use, and secure management scheme.

Figure 2:
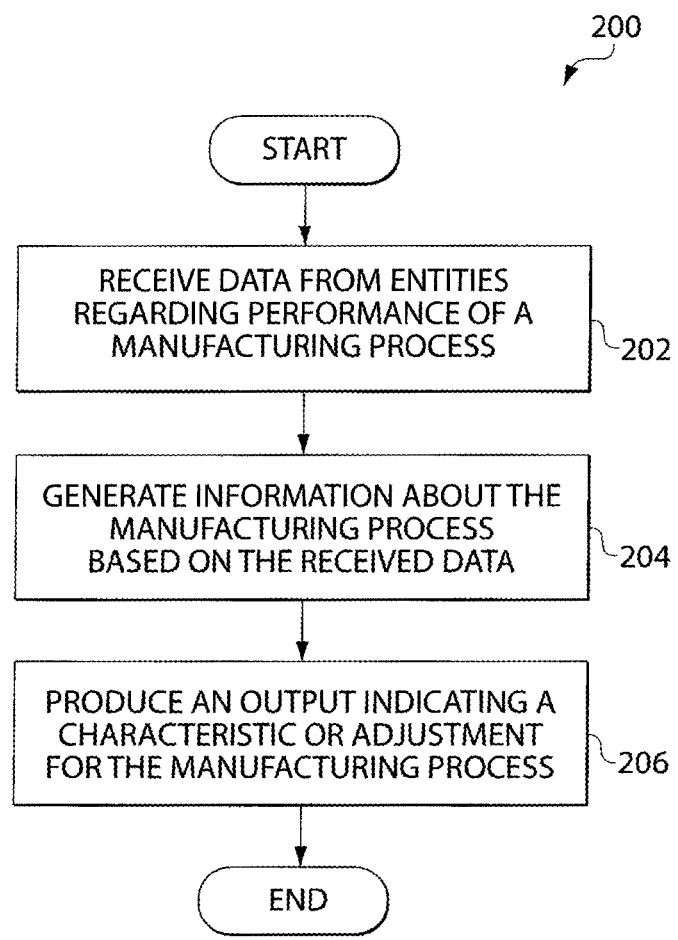
FIG. 2 is a flowchart of a method of managing a pharmaceutical manufacturing process, according to some embodiments.

FIG. 2 is a flow chart of an example of a method 200 of managing a pharmaceutical manufacturing process, according to some embodiments. In step 202, a data processing location (e.g., server 102 in FIG. 1) receives data that is pushed from entities (e.g., entities 106a and 106b in FIG. 1)

regarding performance of a manufacturing process. In some embodiments, the data may be transmitted over Internet communications, and may be formatted as a file. In some embodiments, the data pushing may be a rapid process that may take place as frequently as every few minutes. It should be appreciated, however, that embodiments are not limited to any particular format or timing of data transmission from entities to a server.

In step 204, the received data is analyzed to generate information about the manufacturing process. In some embodiments, the data may be populated into a database (e.g., database 126 in FIG. 1) and may be checked for nonsensical characters, as well as valid specifications (i.e., uncorrupted data and flagged for out of specification alerts on critical parameters). In some embodiments, once the data is received, a message may be sent to a predefined distribution list (e.g., distribution list 132 in FIG. 1), which may comprise customers and/or administrative personnel, to alert individuals and/or entities regarding the status of data in the file received.

The collected data may be further analyzed in step 204 to identify existing and/or potential manufacturing problems. The analyzed data may relate to the manufacturing process and manufacturing entities in any suitable way. It may relate to a portion of the process as performed by multiple entities. Alternatively, it may relate to multiple processes performed by a single entity, etc. For example, the system may be able to identify missing critical batch information in a timely manner. The data processing location (e.g., server 102 in FIG. 1) may receive data pushed from entities periodically (e.g., every few hours, minutes, or seconds, or any suitable time frame), and allow viewing and tracking of processed data to flag initial problems against compared specifications. In some embodiments, real-time reports on trending data may be generated to predict an area of concern before it actually takes place, or to report a situation after an alert.

Such a system may enable rapid and accurate analysis and feedback of data collected from manufacturing facilities, by comparing with specifications to generate information about the manufacturing process. The resulting information may be used to predict issues across sites and/or across batches within a single site. This may enable determining either systemic problems with batches that indicate a problem with the underlying recipe or individual site-specific problems.

In step 206, the system may feedback an output to one or more entities involved in the manufacturing process. The feedback may indicate a characteristic or adjustment for the manufacturing process. A feedback mechanism to the entities may be implemented in any suitable way, such as an electronic information-sharing technique, such as email, population of a collaboration space, or transfer of a report defined by an event, to any appropriate distribution list. In some embodiments, the entities need not have a third party vendor-specific software or hardware client interface installed. Instead, the system may enable simply taking a file generated by the manufacturing facility, in a format determined by its local manufacturing batch process machinery.

Enforcement mechanisms may be used at one or more points in the system to restrict access to data processing location and/or the feedback information. These points may include, for example: protecting computerized instructions (e.g., a recipe for synthesizing a radiopharmaceutical); pushing information into the data processing location; obtaining information from the data processing location, including results on the analysis of the pushed data. In some embodiments, enforcement may be implemented using security keys (e.g., security key 120 in FIG. 1).

Such security measure may be implemented using security keys, using various techniques. Such techniques may preclude electronic access to data in a specific electronic location, unless a valid security key is provided as a credential. Alternatively or additionally, such a technique may involve cryptographic protection of data such that the data may not be decrypted into a human readable or machine usable format without cryptographic processing using a security key. Though, it should be appreciated that other techniques for restricting access to, use of or modification of information may be used and the information used to enable access use or modification may be a "security key." In some embodiments, a security key may be used to restrict pushing of data into the data processing location. For example, receiving data at the data processing location may comprise conditionally receiving the data based on a security key associated with the data. Such a security key may be provided, for example, by the entity that pushed the data using a local security key (e.g., key 120 at entity 106a in FIG. 1). As another example of restricting data pushed to the data processing location, in some embodiments, a security key may be a format converter that enables the data processing location (e.g., server 102 of FIG. 1) to convert generic files pushed from entities into appropriate database entries at the data processing location. The key may be sent by an entity with a data file, or may be programmatically obtained by the data processing location.

Alternatively or additionally, security keys may be used to restrict the output of information that is fed back to entities. For example, in some embodiments, supplying an output to an entity may be conditional based on a security key possessed by the entity. In some embodiments, access to a shared collaboration space (e.g., collaboration space 130) may be restricted by use of at least one security key. As another example, the data processing location may be programmed to distribute a set of instructions specifying modifications to be performed by at least one machine of a manufacturing process; a security key may restrict access to this set of instructions in a format that is executable by the machine. As yet another example, entities may freely access the instructions, but may be restricted in modifying the set of instructions by a security key.

Regardless of the exact nature of the enforcement mechanism, security keys may be used at one or more points in the system to restrict access to the data processing location to only authorized entities. This may enable a scalable and easily manageable security system without necessitating installation of complex software or hardware at various entity sites.

Figure 3:
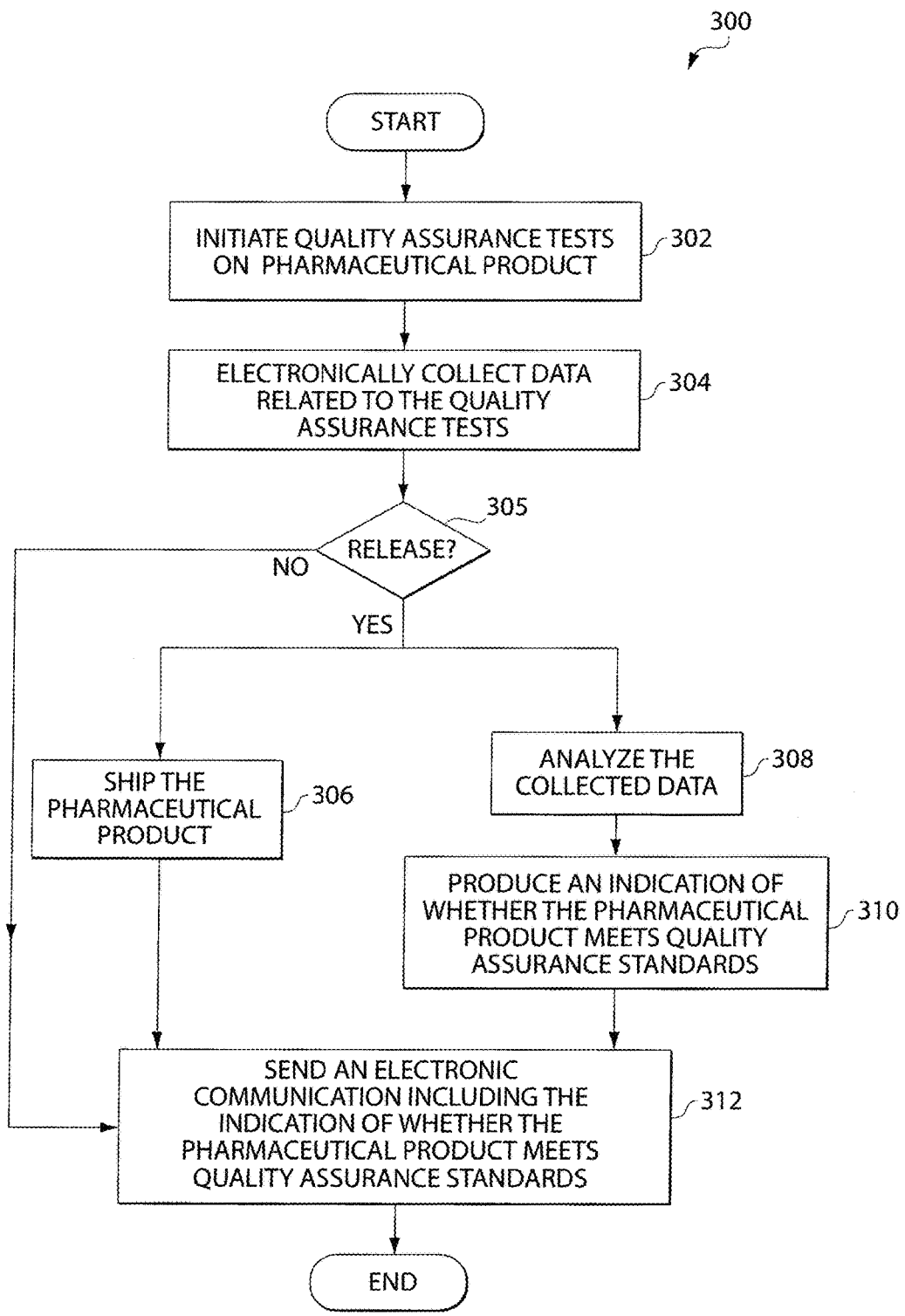
FIG. 3 is a flowchart of a method of dispensing pharmaceutical products that undergo quality assurance tests prior to administration, according to some embodiments.

FIG. 3 is a flow chart of an example of a method 300 of dispensing pharmaceutical products that undergo quality assurance tests prior to administration to patients, according to some embodiments. In some embodiments, it may be desirable to perform quality assurance test on radiopharmaceuticals, to determine suitability for patient administration. In some embodiments, the system may enable shipping pharmaceuticals in advance of one or more steps of quality assurance testing being completed. For example, in some cases, quality assurance testing may comprise one or more tests that require a relatively longer time to complete (e.g., sterility testing, involving growing of organisms, may require several weeks to complete). In such cases, the system may enable shipping pharmaceuticals soon after all applicable tests have passed, been reviewed and labeled for release, but before some of the tests that may take a longer time are completed. This may enable, in some embodiments, a radio pharmacy to timely ship radiopharmaceuticals shortly after applicable testing is completed to provide sufficient lead time for administration to patients at the receiving facilities, while also allowing the same radiopharmaceuticals to be further tested for quality assurance during shipping transit of the pharmaceuticals, and alerting the receiving facilities of the quality of the radiopharmaceuticals once the further testing is complete.

In step 302, if data from an entity (e.g., entity 106a or 106b in FIG. 1) is pushed to a data processing location (e.g., server 102 in FIG. 1) in a timely manner, then the data processing location may initiate quality assurance tests on a pharmaceutical product. In step 304, a data collection location may electronically collect data needed for the quality assurance tests. In some embodiments, the data may be supplied by an entity through a simple generic type of interface.

After data collection is complete, in step 305, there may be a decision made as to whether to release the pharmaceutical product for shipment. In some embodiments, this decision may be based on applicable testing, such as quality assurance testing, on the collected data. Additionally or alternatively, the decision to release may be based on other suitable criteria, decided by any suitable entity, such as a quality assurance organization within a radio pharmacy. Regardless of the exact criteria involved in the decision of step 305, if the pharmaceutical product is deemed ready for release, then in step 306, the pharmaceuticals may be shipped to requesting medical facilities.

While the pharmaceuticals are being shipped, in step 308, the data that was collected may be further analyzed by the data processing location to determine quality assurance. The system may identify missing or invalid data, and may perform one or more quality assurance tests according to predefined specifications. After completing the quality assurance tests, in step 310, the data processing location may produce an indication of whether the pharmaceutical product meets quality assurance standards.

In step 312, the data processing location may send an electronic communication including an indication of whether the pharmaceutical product meets quality assurance standards. This electronic communication may be achieved by any suitable technique, such as posting information to a shared collaboration site, sending an email to a predefined distribution list, or any other suitable type of human readable alert. Regardless of the exact nature of the communication, the data processing location may alert an administration site approving or disapproving use of the shipped pharmaceuticals once the quality assurance analysis of the data is completed.

Figure 4:
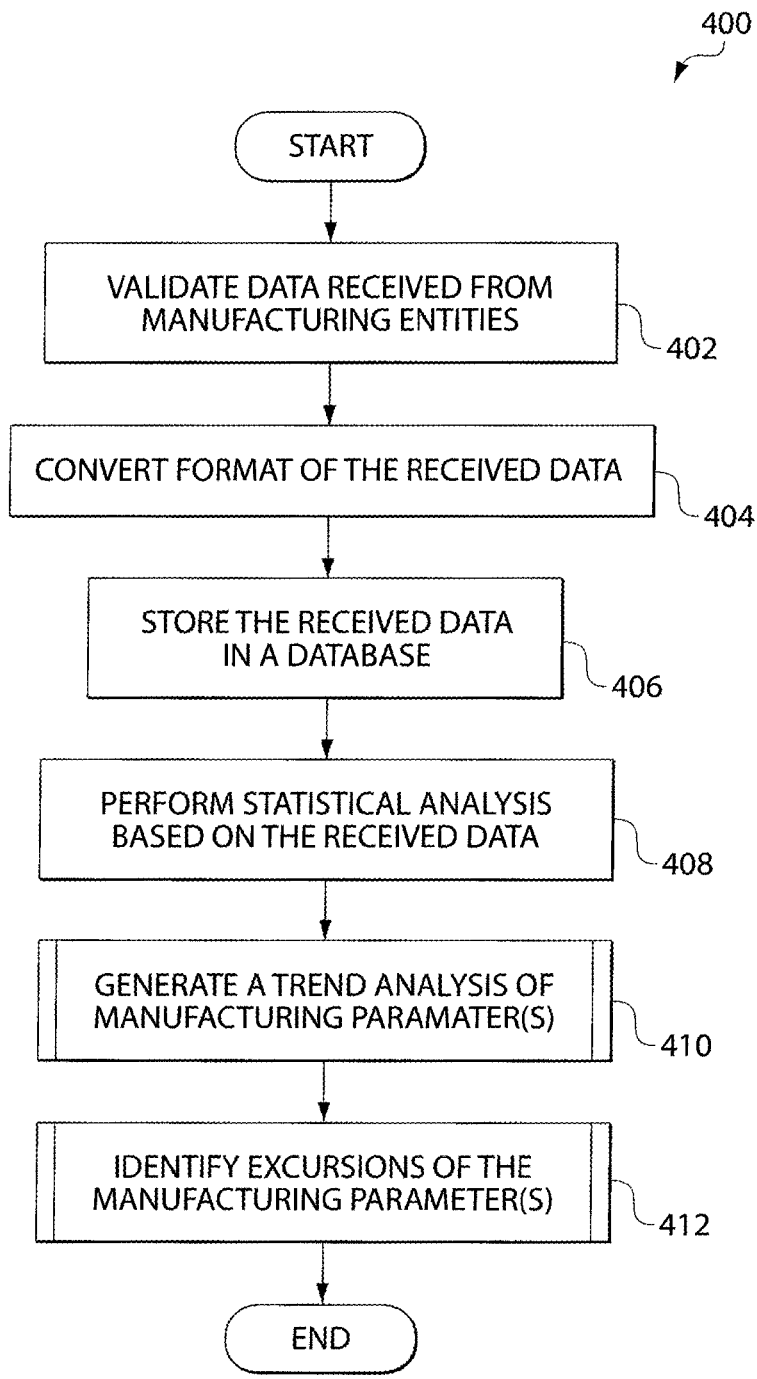
FIG. 4 is a flowchart of a method of analyzing data collected regarding a pharmaceutical manufacturing process, according to some embodiments.

FIG. 4 is a flow chart of an example of a method 400 of analyzing data collected regarding a pharmaceutical manufacturing process, according to some embodiments. In step 402, a data processing location (e.g., server 102 in FIG. 1) may validate that the received data is not corrupted and is in an acceptable format for storage and analysis. If the data indicates an out of specification critical parameter, then the data processing location may generate an alert to an appropriate entity or individual.

In some embodiments, in step 404, when data is collected from a plurality of different entities, the data processing location may convert the collected data into a common format for storage and analysis. In step 406, once the data is correctly formatted, the received data may be stored in a database (e.g., database 126 in FIG. 1).

In step 408, the data processing location may perform statistical analysis on the collected data. The statistical analysis may involve any suitable statistical processing techniques to determine whether the collected data indicates a deviation from an expected or standard set of data. As non-limiting examples, these statistical analysis may involve computing a measure of deviation, such as number of standard deviations away from a mean (e.g., Chebyshev's inequality), or a distributional deviation for multi-sampled data points (e.g., Kullback-Leibler divergence), or a predictive statistical deviation analysis (e.g., Kalman filtering), etc.

In some embodiments, in step 410, the analysis may comprise a trending analysis that may indicate a trend in a parameter of the manufacturing process. As an example, the data processing location may compare the collected data to a set of trending parameters, with a defined number of data collection points of interest, and determine whether the collected data indicates a potential problem. In some cases, the predicted problem may be a systemic problem with the manufacturing process, such as a problem with the underlying recipe for synthesizing the radiopharmaceutical. In such cases, the data processing location may determine an adjustment for a recipe of the radiopharmaceutical synthesis. Alternatively, the predicted problem may indicate a localized problem at a particular facility, in which case instructions may be sent to that facility for modifications.

Regardless of the exact nature of the analysis performed, in step 412, the data processing location may identify/predict excursions of the manufacturing process parameter(s) that may lead to out of specification pharmaceuticals. In general, for the type of statistical analysis techniques used in some embodiments, a larger collection of data from multiple sources typically improves the accuracy of analysis and prediction of such excursions.

In some embodiments, data collected during manufacturing of a completed batch may be used to determine whether to proceed to a next batch. If a risk associated with a problem that occurred during manufacturing of a batch is low, the manufacturing process may proceed to synthesize another batch before an investigation of the problem is completed.

Figure 5:
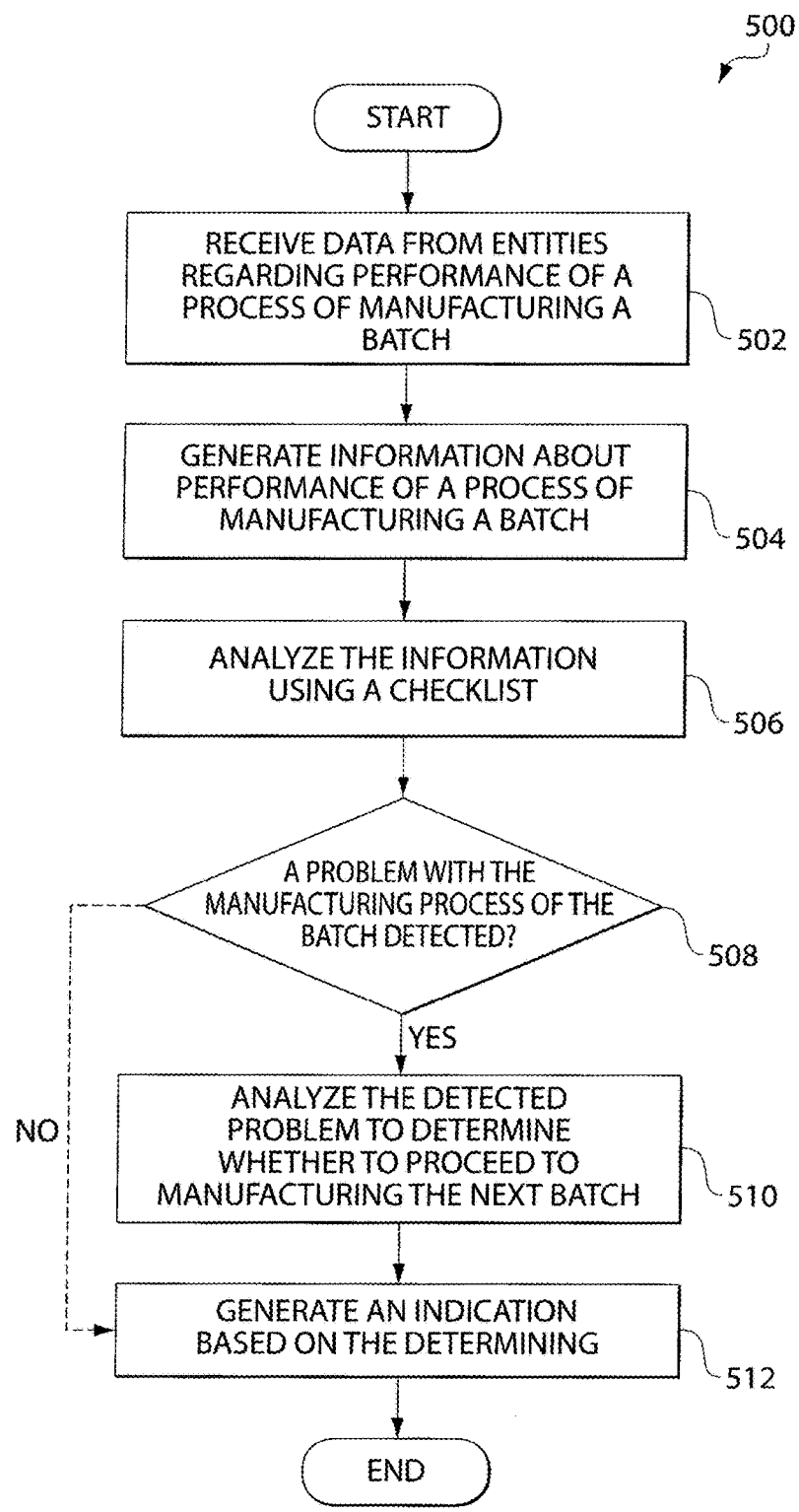
FIG. 5 is a flowchart of a method of analyzing a problem occurred during a manufacture of a batch to determine whether to proceed to a manufacture of a next batch, according to some embodiments.

FIG. 5 illustrates a process 500 of utilizing information about a completed batch of a radiopharmaceutical to determine whether to proceed to manufacture another batch of the radiopharmaceutical or stop a batch manufacturing process. Process 500 may be employed during a batch manufacturing process of any radiopharmaceutical. It may be employed in whole or in part during or after a first process, and typically before start of a subsequent (second) process.

Process 500 may be performed within a short period of time after a completion of a batch, to determine whether it is safe to proceed to manufacture of the next batch within the same order. The time period may comprise, for example, one or more minutes, one or more hours, 24 hours, or any other period of time. In some embodiments, the time period is a range from 0 to 24 hours. Though, it should be appreciated that any other time periods may be utilized, as embodiments of the invention are not limited in this respect.

Process 500 may operate in real-time, which is, in this case, defined as a process in which a decision regarding whether to proceed to manufacture a next batch based on the analysis of information on a performance of a process of manufacture of a prior batch is performed within a short period of time, as part of the batch manufacturing process.

Process 500 may start at any suitable time. Also, process 500 may operate simultaneously with a manufacturing process synthesizing a radiopharmaceutical in batches or may begin executing in response to an indication that a batch is completed. The process may begin executing in response to user input or any other trigger.

At block 502, a data processing location (e.g., server 102 in FIG. 1) receives data that is received from entities (e.g., entities 106a and 106b in FIG. 1) regarding performance of a manufacturing process of a batch. The processing at block 502 may be similar to step 202 (FIG. 2) of receiving data from entities. The data collection may be performed at any point during the manufacture of the batch and may take place frequently. In some embodiments, the data is received after the manufacture of the batch is completed.

Next, at block 504, information about performance of a process of manufacturing a batch of a radiopharmaceutical may be generated. The information may be generated in the same or similar way to generating the information about the manufacturing process in step 204 of FIG. 2. For example, the information may be generated by analyzing data collected from entities, such as, for example, 106a and 106b in FIG. 1. Moreover, in some embodiments, information generated at block 504 based on data received at block 502 may be part of the information generated in step 204 based on data received in step 202.

The generated information may be further analyzed in a suitable manner—for example, using a checklist, at block 504. The analysis of the information about a manufacturing process may involve comparing one or more characteristics of the manufacturing process to known problems which may occur during a synthesis of a radiopharmaceutical. The known problems may be included in the checklist comprising a set of items describing a manufacturing process and intended to be used for investigation of the process. The checklist may be defined in advance in any suitable manner.

The checklist may be used to identify whether a problem has occurred during a manufacture of a batch. In some embodiments, the checklist may be presented on a user interface of a suitable display so that a user (e.g., an operator at a manufacturing facility or any other user) may view the checklist and specify results of an assessment of the manufacturing process. The checklist may comprise a questionnaire or may be presented in any other format.

When a manufacturing facility completes an investigation process driven by the checklist, the facility may generate evidence of a proper investigation that complies with good manufacturing practices (GMP). The evidence may be generated, for example, in a format of a report. The report may provide instructions for the investigation and may include answers to be provided, thus insuring completeness of the GMP investigation process. The responses to each question in the evaluation may be used to generate a value (e.g., a true/false logical, a numeric representation, etc.) for each response. These outputs may then be used in a decision process.

In some embodiments, the assessment of the manufacturing process using the checklist may be performed automatically, or in a way that combines in any suitable manner user input and automatic operations. An example of a checklist is shown in FIG. 8.

Referring back to FIG. 5, the analysis of the information about the performance of the process of manufacturing of the batch may result in determining whether a problem with any aspect of the manufacturing process is detected. Thus, at decision block 508, it may be determined whether a problem with the process of manufacturing of the batch is detected. The problem, or a failure, may comprise one or more problems with reagents, manufacturing equipment, or any other problem.

If it is determined, at decision block 508, that a problem has been detected during the manufacture of the batch, process 500 may follow to block 510 where the detected problem may be analyzed to determine whether to proceed to manufacture the next batch. The analysis that may be performed at block 510 is discussed in more detail below in connection with FIG. 6.

If it is determined, at decision block 508, that no problem has been detected during the manufacture of the batch, process 500 may end. It should be appreciated that, if more batches are to be synthesized, the manufacturing process may then proceed to synthesize the next batch.

The analysis performed at block 510 may be used to generate an indication of whether to proceed to synthesize the next batch, at block 512. The generated indication may be in any suitable format and may indicate to the batch manufacturing process whether to stop or proceed to manufacture the next batch. It should be appreciated that the indication may be generated even if a root cause of the detected problem is not identified.

It should be appreciated that process 500 may continue executing for each batch until all batches in the batch manufacturing process (e.g., batches in an order received by the manufacturing facility) are completed. Process 500 may also execute until the manufacturing process stops when a problem is identified in a prior batch that indicates that a failure that cannot be remedied in a short time period is likely to occur during production of the next batch.

In some embodiments, information collected as a result of the assessment of the manufacturing process of the batch using the checklist may be then analyzed using any suitable analysis method, such as a cause map analysis, decision tree analysis, fault tree analysis, event tree analysis, or any other procedure that combines information on multiple failure modes and makes a statistical assessment of the probability of failure/success. These analysis tools may be used to determine the probability of a problem (interchangeably referred to as a failure) using known, suspected, or eliminated failure modes investigated using the investigation checklist.

The probability assessment may be related to risk assessment analysis performed using tools, such as, for example, Failure Modes Effects Analysis (FMEA), to establish probabilities of failure modes and their safety impact. Using these assessment techniques, an overall probability of a failure during a manufacturing of the next batch may be estimated using a probability assessment tool. The estimated probability of a problem at the next run of the manufacturing process may indicate whether it is justifiable to perform the next run before completing the investigation. The analysis may also indicate additional monitoring or one or more remediation measures that may be required for the next run, based on the FMEA requirements.

In some embodiments, regardless of an approach that is used for analysis operations at blocks 506-510, an output of the analysis may be a value indicating a probability of a failure of the manufacturing process during a manufacture of the next batch, as well as values indicating probabilities of failures at different potential failure modes. These values may then be used to determine whether it is recommended for the manufacturing facility to proceed to a next run or indicate that a full investigation is required prior to the next production run. The decision to proceed may be made when no cause of the detected problem is identified and may be based, for example, on FMEA. In this way, the decision to proceed to a next batch may be made when no root cause of the detected problem is identified.

In some embodiments, the analysis of the problem that occurred during the manufacture of the completed batch may be used to determine whether to proceed to synthesize the next batch. As a result of the analysis, a risk value may be determined indicating an assessed risk of proceeding with the synthesis of the next back given the failure at a preceding batch. The analysis may also indicate whether the problem may be remedied in a timely manner before the production of the next batch begin so that all batches are synthesized on time for being delivered and administered to patients.

An assessed risk may indicate how likely a problem is to occur during the manufacture of the next batch given the detected problem during the production of the preceding batch. If the assessed risk is low and/or the problem may be remedied before a beginning of the manufacturing of the next batch, it may be determined that the batch manufacturing process may proceed to the next batch. In some embodiments, when the assessed risk is low, the batch manufacturing process may proceed to the next batch and the investigation and/or mitigation of the detected problem may take place during a synthesis of the next batch. Further, even if the assessed risk is higher but may be remedied before the beginning of the manufacturing of the next batch, it may be determined that the batch manufacturing process may proceed to the next batch. However, if the assessed risk is high and it is determined that it is not feasible to investigate and remedy the detected problem within a short period of time, it may be determined that the batch manufacturing process may need to stop.

Figure 6:
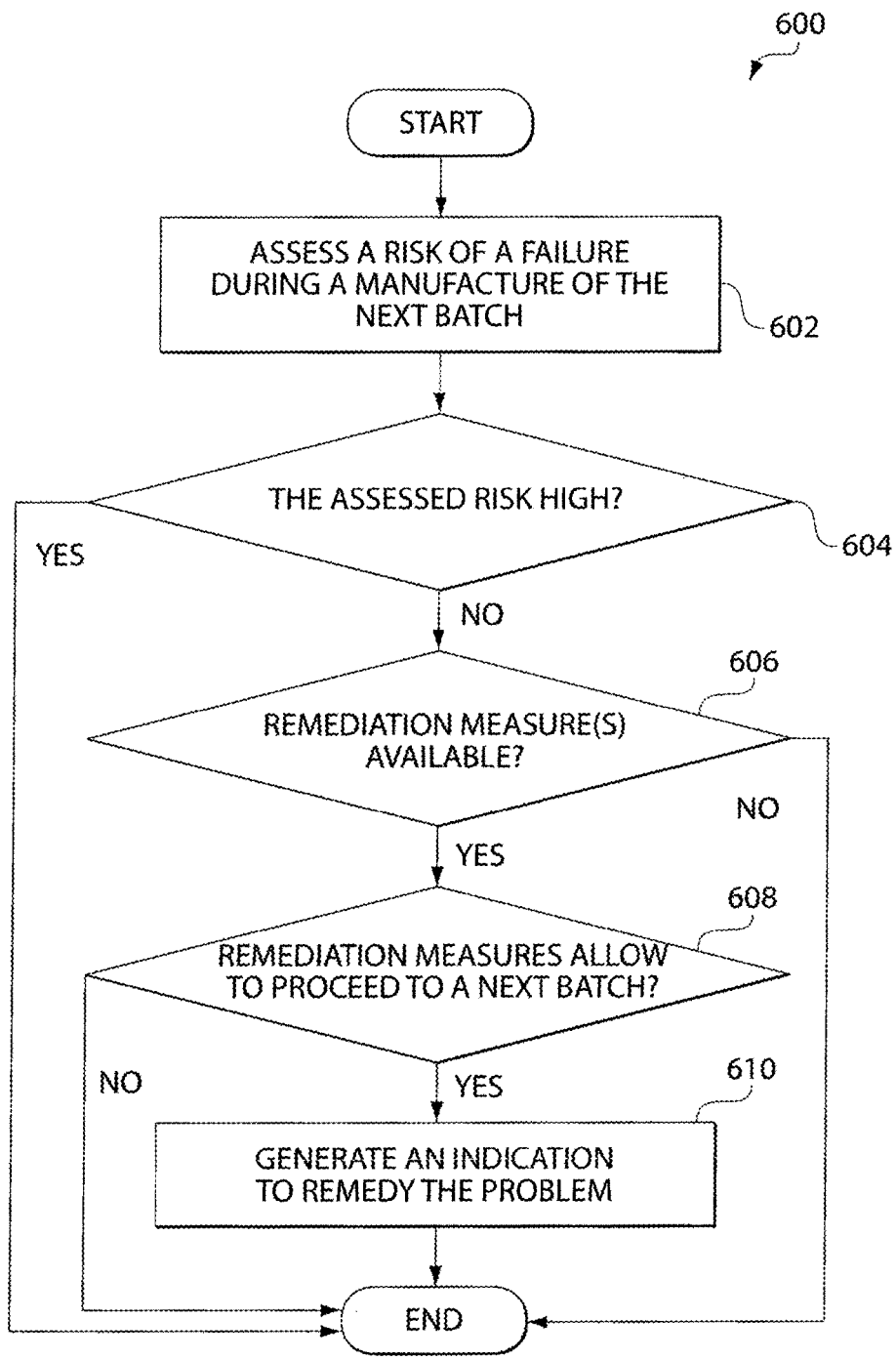
FIG. 6 is another flowchart of the method of analyzing a problem occurred during a manufacture of a batch to determine whether to proceed to a manufacture of a next batch, according to some embodiments.

FIG. 6 illustrates in more detail a process 600 of analysis of the detected problem at block 510. At block 602, a risk of a failure during a manufacture of a next batch may be assessed based on the analysis of information on a performance of the manufacturing process of a prior batch. Next, at decision block 604, it may be determined whether the assessed risk is high. The assessed risk may be represented with a numerical value. This determination may be performed in any suitable manner—for example, a threshold may be defined so that if the assessed risk is greater that the threshold, the risk is identified as high. Any suitable threshold may be utilized which may be defined, for example, based on analyzing a cause map or in any other manner. The threshold and the risk may be represented as numerical values or any other types of values. In some cases, the assessed risk may be represented as a qualitative value.

If it is determined, at block 604, that the assessed risk is high, process 600 may end. In this case, an indication may be generated indicating that the batch manufacturing process should not proceed to a next batch, at block 512 of FIG. 5. Additionally, though not shown in FIG. 6, it may further be determined what investigation may be required and what remediation measures are available to remedy the high-risk failure. The investigation may then be conducted and the manufacturing process may be adjusted to prevent further problems.

If it is determined at block 604, that the assessed risk is not high, process 600 may continue to decision block 606 where it may be determined whether one or more remediation measures are available. The remediation measures may be used to remedy the problem that occurred during the manufacturing of the prior batch, which may prevent a failure during manufacturing of the next batch. The remediation measures may be obtained from a database or any other suitable storage. The remediation measures may be stored in associated with another related information, such as, for example, potential problems that may be encountered during a process of manufacturing a batch (e.g., problems specified in the checklist). The potential problems may be stored in one or more suitable data structures in association with one or more remediation measures intended to remedy the problems, risks associated with the potential problems and any other suitable information. The risks may comprise an expected risk when the remediation measure is performed to remedy the problem, a risk when the remediation measure is not performed, and any other risks. An example of such data structure is the data capture forms provided in FIGS. 12 and 13. The data capture form in this example may include other information, as discussed in more detail below.

If it is determined that the remediation measures are available, process 600 may continue to decision block 608 where it may further be determined whether the available remediation measures allow to proceed to a next batch. Such remediation measures may be completed within a short time period so that the synthesis of the next batch may begin in a timely manner (e.g., within one or more minutes, one or more hours, or within 24 hours from the completion of the prior batch).

Remediation measures may comprise any suitable remediation measures, as embodiments of the invention are not limited in this respect. For example, in some embodiments, the remediation measures may comprise measures that may allow continuing to synthesis of a next batch may include making fresh reagents, using a different lot of SepPak, using a different lot of a QMA cartridge, making a fresh DSP solution, using a fresh bottle of Ascorbic acid USP, using a fresh bottle of Acetonitrile, resetting software, washing semi-prep high-performance liquid chromatography (HPLC) column, making fresh semi-prep mobile phase, correcting mistaking of using a semi-prep wash solution instead of a semi-prep mobile phase, checking and insuring vacuum is working correctly, and any other satiable measures. It should be appreciated that these remediation measures are shown by way of example only, as any remediation measures may be utilized.

When it is determined, at decision block 608, that the available remediation measures do not allow proceeding to the next batch, process 600 may end and follow back to block 512 in FIG. 5. Examples of remediation measures that may prevent continuing to a synthesis of a next batch may include investigating a vacuum failure, a heating failure, a leak in cassette or a valve failure, or any other satiable measures. Such measures may be required when, for example, it was determined for the prior run of the manufacturing process that a drug substance precursor contains impurities, DSP is beyond expiry and a second lot is not available, GC system is not operational and HPLC radiation detector is operating correctly. It should be appreciated that these remediation measures are shown by way of example only, as any remediation measures may be substituted.

When it is determined, at decision block 608, that the available remediation measures allow proceeding to the next batch, process 600 may continue to block 610 where an indication of a remediation may be generated for the manufacturing process, an operator of a manufacturing facility (e.g., a PMF), or to any other entity that may perform the remediation. The indication may be generated in any suitable manner.

The remediation may take place before a beginning of the manufacture of the next batch. In some embodiments, the remediation may take place during the process of manufacturing of the next batch, if a failure of the manufacturing process is determined to be unlikely and/or if the risk posed by this failure is low and does not affect quality of the radiopharmaceutical.

If it is determined that the remediation measures are not available, process 600 may end. Because in this case the assessed risk of a failure is low, an indication may be generated indicating that the batch manufacturing process may proceed to a next batch, at block 512 of FIG. 5.

In some embodiments, a report may be generated based on results of the analysis of the detected problem, including assessment of the problem using the checklist, information on performed or intended investigation, intended or performed remediation measures and any other suitable information. The report may be generated based on GMP and may be used by the manufacturing facility as evidence of its compliance with GMP.

Thus, the described techniques may improve efficiency of operation and management of a radiopharmaceutical manufacturing facility. Furthermore, the techniques may help decrease costs and generate revenue.

Figure 7:
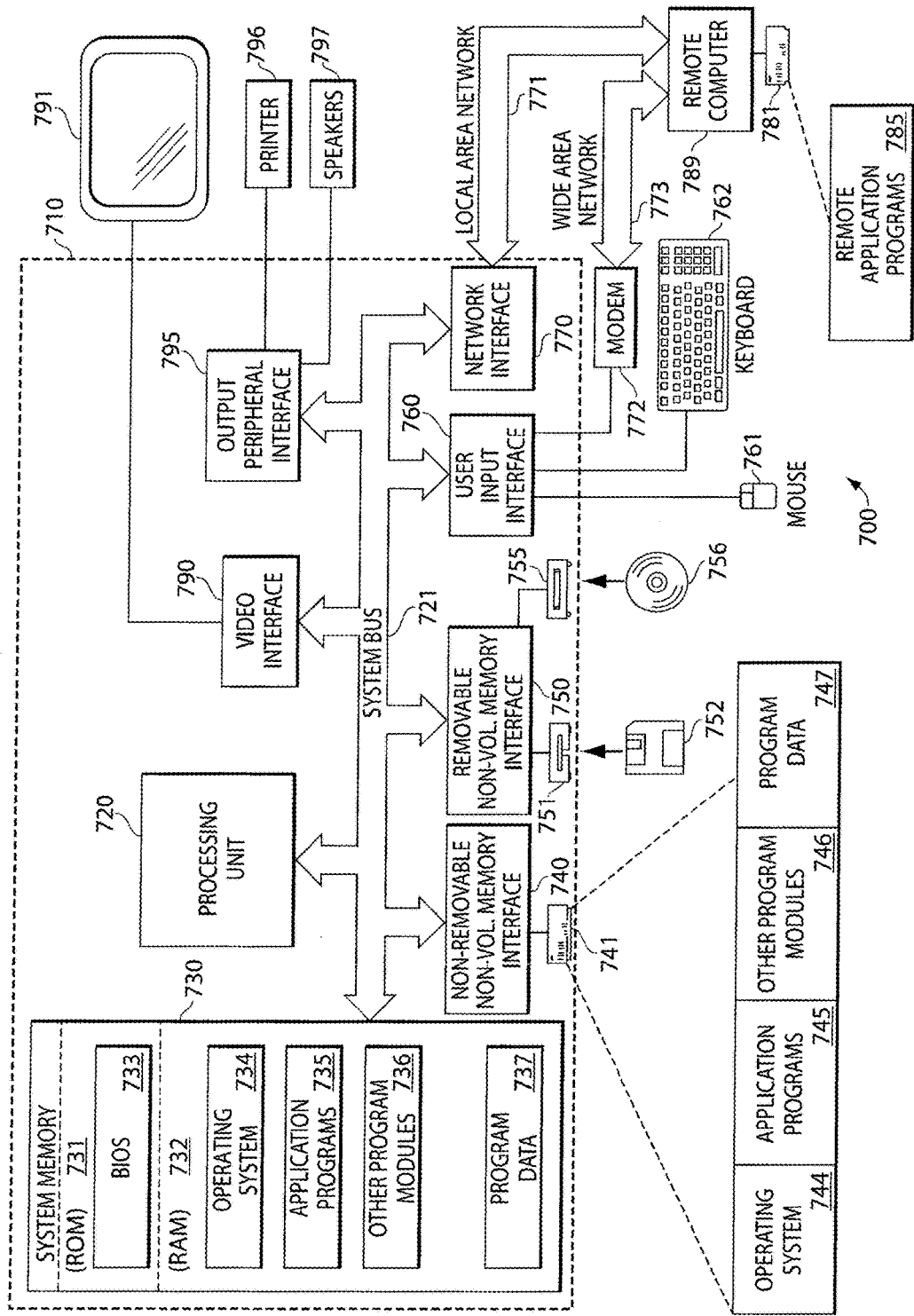
FIG. 7 is a schematic illustration of a representative computing device on which embodiments of the invention may operate.

FIG. 7 illustrates an example of a suitable computing system environment 700 on which the invention may be implemented. This computing system may be representative of a computing system that collects, analyzes, and/or provides feedback regarding a pharmaceutical manufacturing process (e.g., server 102 in FIG. 1). However, it should be appreciated that the computing system environment 700 is only one example of a suitable computing environment and is not intended to suggest any limitation as to the scope of use or functionality of the invention. Neither should the computing environment 700 be interpreted as having any dependency or requirement relating to any one or combination of components illustrated in the exemplary operating environment 700.

The invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments or cloud-based computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 7, an exemplary system for implementing the invention includes a general purpose computing device in the form of a computer 710. Components of computer 710 may include, but are not limited to, a processing unit 720, a system memory 730, and a system bus 721 that couples various system components including the system memory to the processing unit 720. The system bus 721 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 710 typically includes a variety of computer readable media. Computer readable media can be any available media that can be accessed by computer 710 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 710. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 730 includes computer storage media in the form of volatile and/or nonvolatile memory such as read only memory (ROM) 731 and random access memory (RAM) 732. A basic input/output system 733 (BIOS), containing the basic routines that help to transfer information between elements within computer 710, such as during start-up, is typically stored in ROM 731. RAM 732 typically contains data and/or program modules that are immediately accessible to and/or presently being operated on by processing unit 720. By way of example, and not limitation, FIG. 7 illustrates operating system 734, application programs 735, other program modules 736, and program data 737.

The computer 710 may also include other removable/non-removable, volatile/nonvolatile computer storage media. By way of example only, FIG. 7 illustrates a hard disk drive 741 that reads from or writes to non-removable, nonvolatile magnetic media, a magnetic disk drive 751 that reads from or writes to a removable, nonvolatile magnetic disk 752, and an optical disk drive 755 that reads from or writes to a removable, nonvolatile optical disk 756 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 741 is typically connected to the system bus 721 through an non-removable memory interface such as interface 740, and magnetic disk drive 751 and optical disk drive 755 are typically connected to the system bus 721 by a removable memory interface, such as interface 750.

The drives and their associated computer storage media discussed above and illustrated in FIG. 7, provide storage of computer readable instructions, data structures, program modules and other data for the computer 710. In FIG. 7, for example, hard disk drive 741 is illustrated as storing operating system 744, application programs 745, other program modules 746, and program data 747. Note that these components can either be the same as or different from operating system 734, application programs 735, other program modules 736, and program data 737. Operating system 744, application programs 745, other program modules 746, and program data 747 are given different numbers here to illustrate that, at a minimum, they are different copies. A user may enter commands and information into the computer 710 through input devices such as a keyboard 762 and pointing device 761, commonly referred to as a mouse, trackball or touch pad. Other input devices (not shown) may include a microphone, joystick, game pad, satellite dish, scanner, or the like. These and other input devices are often connected to the processing unit 720 through a user input interface 760 that is coupled to the system bus, but may be connected by other interface and bus structures, such as a parallel port, game port or a universal serial bus (USB). A monitor 791 or other type of display device is also connected to the system bus 721 via an interface, such as a video interface 790. In addition to the monitor, computers may also include other peripheral output devices such as speakers 797 and printer 796, which may be connected through a output peripheral interface 795.

The computer 710 may operate in a networked environment using logical connections to one or more remote computers, such as a remote computer 780. The remote computer 780 may be a personal computer, a server, a router, a network PC, a peer device or other common network node, and typically includes many or all of the elements described above relative to the computer 710, although only a memory storage device 781 has been illustrated in FIG. 7. The logical connections depicted in FIG. 7 include a local area network (LAN) 771 and a wide area network (WAN) 773, but may also include other networks. Such networking environments are commonplace in offices, enterprise-wide computer networks, intranets and the Internet.

When used in a LAN networking environment, the computer 710 is connected to the LAN 771 through a network interface or adapter 770. When used in a WAN networking environment, the computer 710 typically includes a modem 772 or other means for establishing communications over the WAN 773, such as the Internet. The modem 772, which may be internal or external, may be connected to the system bus 721 via the user input interface 760, or other appropriate mechanism. In a networked environment, program modules depicted relative to the computer 710, or portions thereof, may be stored in the remote memory storage device. By way of example, and not limitation, FIG. 7 illustrates remote application programs 785 as residing on memory device 781. It will be appreciated that the network connections shown are exemplary and other means of establishing a communications link between the computers may be used.

Having thus described several aspects of at least one embodiment of this invention, it is to be appreciated that various alterations, modifications, and improvements will readily occur to those skilled in the art.

The described technique may be applied to any suitable manufacturing process of any radiopharmaceutical. An exemplary manufacturing process may include manufacturing of Positron Emission Tomography (PET) drug produced in a PET PMF using an automated Chemical Synthesis Unit (CSU). The CSU manages an introduction of $^{18}F-$ into the reactor, azeotropic removal of water, introduction of the drug substance precursor (DSP), reaction condition control (temperature and pressure), purification by semi-preparative high-performance liquid chromatography (HPLC), solvent exchange on a SepPak, formulation of the drug product, and final sterile filtration. These steps may be performed using valves, gas flow, vacuum pumps, fluid pumps, heaters, radiation detectors, UV detectors, and various forms of tubing. Given the complexity of the operations and the mechanical components involved in the manufacture if PET drugs, there are numerous points of potential malfunction, failure, or operator errors.

The short half-life of $^{18}F$ PET drug products requires that their production occur near a site of use. A production of a PET drug may be complete approximately 1 hour after delivery of $^{18}F$ from a cyclotron to the CSU. Testing and release of the bulk drug product may be completed approximately 1 hour after production. Testing may include a determination of impurities (radioactive and non-radioactive by HPLC), determination of activity (mCi/mL, by Capintec® dose calibrator), endotoxin determination (by PTS™), and radioactive decay ($t_{1/2}$ by Capintec®). There may be multiple points in the testing at which a problem may occur—e.g., an operation may be performed not correctly, equipment may fail, an error due to operator actions may happen, etc.

PET drug products are produced under good manufacturing practices (GMPs), such as, for example, 21 CFR Part 212, "Current Good Manufacturing Practice for Positron Emission Tomography Drugs." The GMPs require the investigation of deviations, equipment failures, aberrant or failing test results, and operator errors, to mention a few. Investigations are expected to identify root causes and establish corrective and preventative actions (CAPA) to eliminate or decrease the probability of future failures Completing investigations in a suitable timeframe to support ongoing operations in the PMF may present a significant challenge. A typical facility may produce several (e.g., three) lots a day, and the ability to complete a comprehensive investigation in time to allow production of a next scheduled production lot is challenging and generally not feasible. Several factors contribute to the challenge of completing investigations on the same day—for instance, the CSU has residual radioactivity from the synthesis, and cannot typically be examined for the purpose of trouble shooting until the next day. Accordingly, the described techniques may be used to, when one batch is completed, determine in a timely manner whether the manufacturing process may proceed to a next batch. An example of a checklist that may be used for analysis of information received during a manufacture of a batch of a PET pharmaceutical is shown in FIG. 8.

Figure 9:
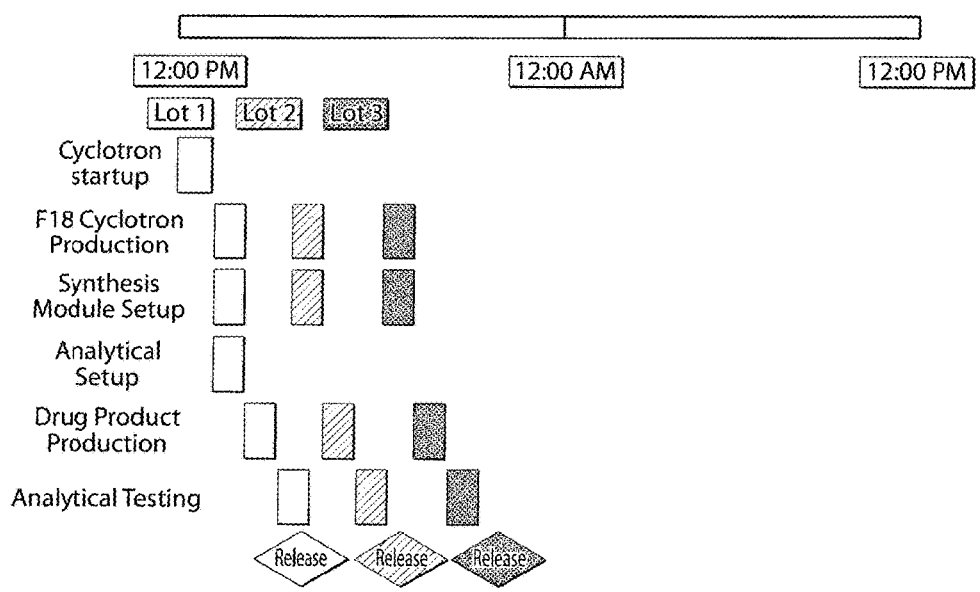
FIG. 9 is a sketch illustrating a timing of a batch production within a day, in accordance with one embodiment.

As another example, FIG. 9 illustrates a timing of a batch production within a day. In FIG. 8, a failure in Batch 1 impacts production of Batches 2 and 3 and may affect, in this example, 40 patients or more if Batch 2 and Batch 3 cannot be produced. In this example, a maximum life of the product is 12 hours post-synthesis, of which 1 hour is Quality Control/release time, and 2 hours or more may be required to get the product to the clinical site. It thus may be required to make a decision as quickly as possible.

FIGS. 12 and 13 comprise examples of a data capture form. In the data capture, investigation check boxes result in a true/false logic. A second column of Form 2 (low chemical yield) in FIG. 13 shows an exemplary assigned risk value if no mitigation is performed, a risk value for the next lot to fail if the failure is ascribed to the individual item if it is identified as a failure, and an assigned risk when no remediation is performed. The next column is a suggested remediation measure which may be represented as a textual or numerical value, or in any other suitable format. The following column may be used to receive input indicating whether the remediation was performed. The following columns indicate an assessed risk value if the suggested remediation is performed and an assigned risk after the mitigation is performed.

The form indicates a probability that an item may be a source of the problem. For items associated with a higher risk, one or more mitigation measures may be defined. The next run may proceed based on the one or more mitigations. In some embodiments, if the identified problem requires fixing hardware, a test run may be performed before proceeding to manufacture a radiopharmaceutical. Further, more than one risk values may be associated with a problem, depending on whether or not a recommended mitigation is to be performed.

In some embodiments, a report may be generated based on the data capture form that may list identified risks, suggested mitigations, whether mitigations were performed, current risk assigned, and an underlying logic that would determine whether to proceed to the next batch based on the risk assigned.

Figure 10:
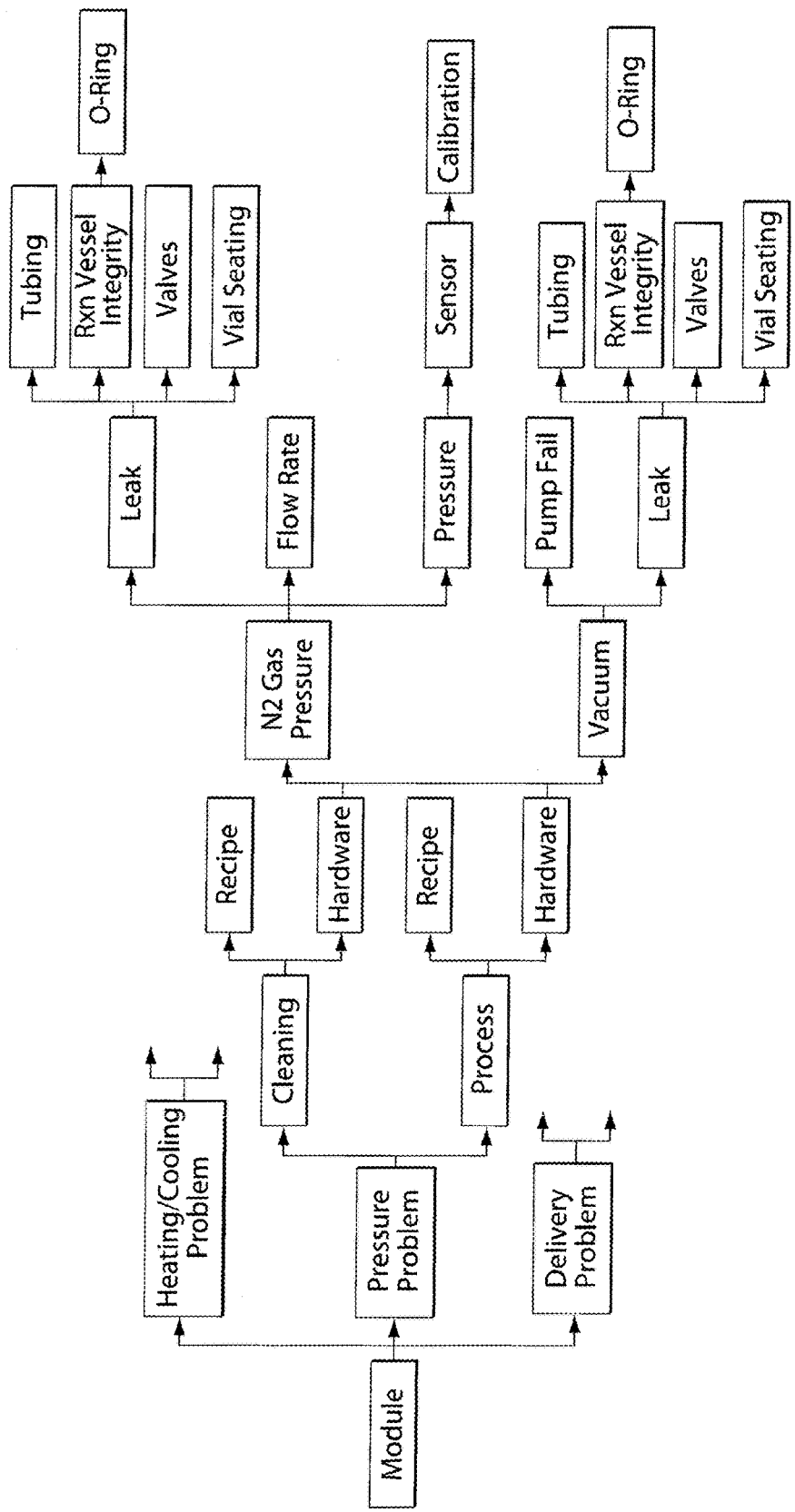
FIG. 10 illustrates a sketch of an example of a cause map, in accordance with one embodiment.

FIG. 10 illustrates an example of a cause map in accordance with one embodiment. At full commercial production, a typical day will include production of three Flurpiridaz $F^{18}$ batches. Batch production begins around midnight when the cyclotron engineer turns on the cyclotron and brings it online for production of $^{18}F$.

Approximately an hour later a target is filled with $O^{18}$ water, and bombardment initiated in the cyclotron to produce $^{18}F$ for use in the first production run. Between 1 and 2 hours later, the $^{18}F$ is delivered to the synthesis module and synthesis is initiated. Prior to this, the synthesis module is setup (reagents and ancillary components installed) for the first synthesis. Similarly, the analytical procedures are setup, including the analytical HPLC which requires system suitability studies be performed prior to the analysis. Drug product production takes approximately 1 hour, followed by 1 hour of analytical testing culmination in the release of the bulk product. In the meantime, Batch 2 synthesis is initiated. The first steps being production of $^{18}F$ in the cyclotron, and setup of a second synthesis module. Analytical setup has already been completed and does not need to be repeated. The second batch is produced, then tested, and ultimately released. As with the second batch, setup of the synthesis module for production of the third batch is typically initiated before release of the second batch.

Figure 11:
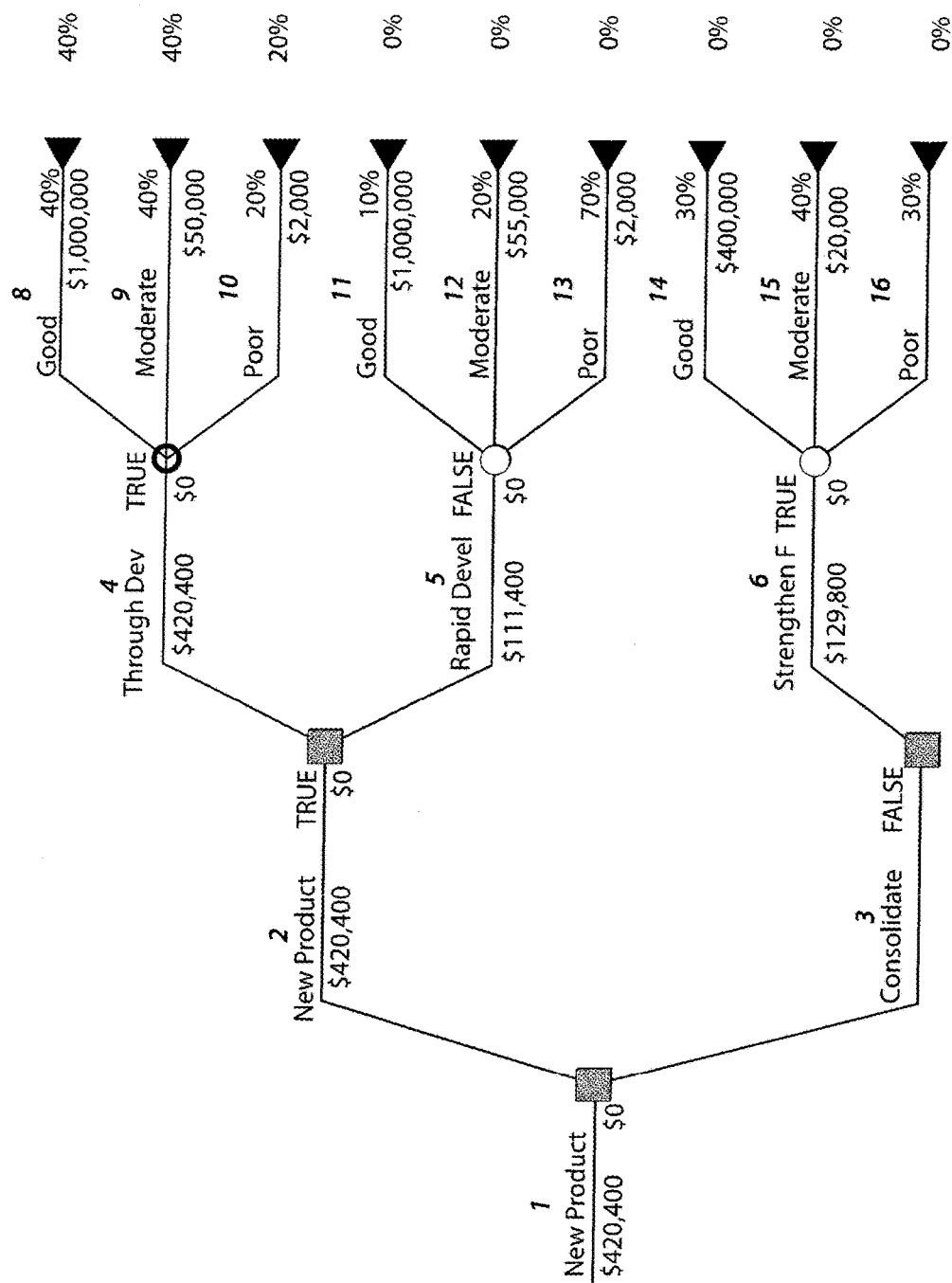
FIG. 11 illustrates an example of an analysis of a problem detected during a manufacturing process of a batch using a decision tree approach, in accordance with one embodiment.

As another example, as disused above, an analysis of the problem detected during a manufacturing of a batch (e.g., as shown at block 510 in FIG. 5) may be performed in any suitable manner. FIG. 11 illustrates an example of an analysis using a decision tree approach. In this example, the decision tree analysis uses nodes for each aspect of failure mode(s) that are evaluated. Each node has an associated probability of occurrence. The probability may be determined by reference to values in a checklist used for investigation, in conjunction with an FMEA which is used for analyzing potential failure modes at a manufacturing facility, assessing a likelihood of each failure mode and assigning a severity to the failure. Thus, in this exemplary approach, a look up table of probability values may be associated with each node of the decision tree.

It should be appreciated that, even though the techniques of determining whether to proceed to a next batch are described in connection with a process of manufacturing radiopharmaceuticals, it should be appreciated that the techniques may be employed for manufacturing of any other pharmaceuticals. For example, the techniques may be employed at facilities where the timing of production may require a decision ahead of completing a full investigation that achieves the identification of a root cause of a problem.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of manufacturing a radiopharmaceutical, the method comprising:
at a data processing location, receiving data from a plurality of entities associated with a plurality of manufacturing facilities, the plurality of entities including a first manufacturing facility that produces a chemical compound and a second manufacturing facility that synthesizes the radiopharmaceutical using the chemical compound produced by the first manufacturing facility, wherein:
each of the plurality of entities performs a portion of a manufacturing process for producing the radiopharmaceutical, and
the data received from a respective one of the plurality of entities relates to performance of a respective portion of the manufacturing process by the respective entity; with at least one processor at the data processing location:
generating information about the manufacturing process based on the received data, the information including an assessment of production of the chemical compound by the first manufacturing facility;
determining, based on the generated information, a problem with the manufacturing process in producing the chemical compound and a risk value, the risk value indicating a risk of proceeding with the manufacturing process with the problem present;
comparing the risk value to a threshold risk value;
based on determining that the risk value is greater than the threshold risk value:
providing an indication to stop the manufacturing process for producing the radiopharmaceutical; and
based on determining that the risk value is less than the threshold risk value:
outputting an indication to adjust at least a portion of the manufacturing process performed by the first entity, the adjustment comprising a change in a recipe for producing the chemical compound; and
providing an indication to continue the manufacturing process for producing the radiopharmaceutical.

2. The method of claim 1, wherein:
generating information about the manufacturing process comprises generating an indication of a trend in a parameter of the manufacturing process.

3. The method of claim 2, wherein:
the data comprises data associated with a plurality of batches of a pharmaceutical compound manufactured at facilities associated with multiple entities of the plurality of entities.

4. The method of claim 1, wherein:
the indication to adjust the at least a portion of the manufacturing process comprises an indication to adjust a parameter of the manufacturing process.

5. The method of claim 1, further comprising:
outputting an indication of the problem with the manufacturing process with the at least one processor.

6. The method of claim 5, wherein:
generating information about the manufacturing process comprises generating a trend analysis of at least one parameter of the manufacturing process based on data collected from entities of the plurality of entities.

7. The method of claim 5, wherein:
the problem comprises a systemic problem with the manufacturing process.

8. The method of claim 7, further comprising:
with the at least one processor, generating the information about the manufacturing process with the at least one processor based on data associated with a plurality of batches of a pharmaceutical compound manufactured at facilities associated with multiple ones of the plurality of entities.

9. The method of claim 1, wherein:
generating the information about the manufacturing process comprises at least one of:
performing a statistical analysis, or
identifying an excursion of a parameter of the manufacturing process that lead to an out of specification radiopharmaceutical.

10. The method of claim 1, wherein:
receiving data from the plurality of entities comprises receiving data pushed from each of the plurality of entities.

11. The method of claim 1, wherein:
generating information comprises populating a database with data received from the plurality of entities.

12. The method of claim 11, further comprising:
with the at least one processor, validating the data before storing the data in the database such that corrupted data is not stored in the database.

13. The method of claim 12, wherein validating further comprises generating an alert when the data indicates a parameter associated with the manufacturing process is out of specification.

14. The method of claim 11, further comprising:
converting data from entities of the plurality of entities into a common format with the at least one processor before storing the data in the database.

15. The method of claim 1, further comprising:
with the at least one processor, electronically routing a message containing an indication of the determined problem to a stored distribution list.

16. The method of claim 1, wherein:
receiving the data from the plurality of entities comprises:
receiving the data over a computer communication network, or
receiving the data formatted as a plurality of files from the plurality of entities.

17. The method of claim 1, wherein:
receiving the data from an entity of the plurality of entities comprises conditionally receiving the data based on a security key associated with the entity.

18. The method of claim 1, further comprising:
outputting the indication to adjust the at least a portion of the manufacturing process to an entity of the plurality of entities with the at least one processor based on a security key associated with the entity.

19. The method of claim 17, wherein:
the indication to adjust the at least a portion of the manufacturing process comprises information defining a modification to the manufacturing process.

20. A system for manufacturing a radiopharmaceutical, the system comprising:
a database configured to store data;
at least one processor connected to a network, wherein the processor is programmed to:
receive data from each of a plurality of entities including a cyclotron for producing a chemical compound and a synthesis module that uses the chemical compound to synthesize the radiopharmaceutical, wherein:
each of the plurality of entities performs a portion of a manufacturing process for producing the radiopharmaceutical, and
the data from a respective one of the plurality of entities relates to performance of a respective portion of the manufacturing process performed by the respective entity;
store at least part of the received data in the database;
generate information about the manufacturing process using the stored data, the information comprising an assessment of production of the chemical compound by the cyclotron and delivery of the chemical compound to the synthesis module;
determine, based on the generated information, a problem with the production of the chemical compound by the cyclotron and/or delivery of the chemical compound to the synthesis module and a risk value, the risk value indicating a risk of proceeding with the manufacturing process with the problem present;
compare the risk value to a threshold risk value;
based on determining that the risk value is greater than the threshold risk value:
provide an indication to stop the manufacturing process for producing the radiopharmaceutical; and
based on determining that the risk value is less than the threshold risk value:
output an indication to adjust the production of the chemical compound by the cyclotron and/or a mitigation for the failure in delivery of the chemical compound to the synthesis module; and
provide an indication to continue the manufacturing process for producing the radiopharmaceutical.

21. At least one non-transitory computer-readable storage medium comprising computer-executable instructions that, when executed by at least one processor, performs a method comprising:
receiving data from a plurality of entities including a first entity that produces a chemical compound and a second entity that uses the chemical compound to synthesize the radiopharmaceutical, wherein each of the plurality of entities performs a portion of a manufacturing process for producing the radiopharmaceutical, and wherein the data received from a respective one of the plurality of entities relates to a respective portion of the manufacturing process performed by the respective entity;
accessing a data store comprising information about a plurality of problems that may occur with producing the chemical compound and synthesis of the radiopharmaceutical using the chemical compound and, for each of the plurality of problems, a mitigation for addressing the problem, and a risk value;
generating information about the manufacturing process based on the received data, the information comprising an assessment of one or more reagents used for producing the chemical compound and/or synthesizing radiopharmaceutical;

determining, based on the generated information, occurrence of a problem of the plurality of problems with the manufacturing process and a risk value associated with the problem, the risk value indicating a risk of proceeding with the manufacturing process with the problem present;

comparing the risk value to a threshold risk value;

based on determining that the risk value is greater than the threshold risk value, providing an indication to stop the manufacturing process for producing the radiopharmaceutical; and based on determining that the risk value is less than the threshold risk value:

outputting an indication of a mitigation associated with the problem to adjust at least a portion of the manufacturing process performed by at least one of the plurality of entities; and providing an indication to continue the manufacturing process for producing the radiopharmaceutical.

22. A system for manufacturing a radiopharmaceutical, the system comprising:

a database configured to store a plurality of problems that may occur with producing a chemical compound and synthesis of the radiopharmaceutical using the chemical compound and, for each of the plurality of problems:

a first risk value indicating a risk if the problem is not mitigated; and a second risk value indicating a risk if the problem is ascribed to a failure;

a processor connected to a network, wherein the processor is programmed to:

receive, via the network, data from each of a plurality of entities for producing the radiopharmaceutical, the plurality of entities including a cyclotron for producing the chemical compound and a synthesis module that uses the chemical compound to synthesize the radiopharmaceutical, wherein:

each of the plurality of entities performs a portion of a manufacturing process for producing the radiopharmaceutical; and the data from a respective one of the plurality of entities relates to performance of a respective portion of the manufacturing process performed by the respective entity;

determine, based on the received data, occurrence of one of the plurality of problems with the production of the chemical compound by the cyclotron and/or synthesis of the radiopharmaceutical by the synthesis module;

determine an assessed risk value associated with occurrence of the problem at least in part by:

setting the assessed risk value to the first risk value stored in the database for the problem based on a determining that the problem is not ascribed to a failure; and setting the assessed risk value to the second risk value stored in the database for the problem based on determining that the problem is ascribed to the failure;

compare the assessed risk value to a threshold risk value;

output an indication to stop the manufacturing process for producing the radiopharmaceutical based on determining that the assessed risk value is greater than the threshold risk value; and output an indication of a mitigation to the problem and an indication to continue the manufacturing process for producing the radiopharmaceutical based on determining that the assessed risk value is less than the threshold risk value.

* * * * *